United States Patent
Bly et al.

(10) Patent No.: US 8,116,841 B2
(45) Date of Patent: Feb. 14, 2012

(54) ADHERENT DEVICE WITH MULTIPLE PHYSIOLOGICAL SENSORS

(75) Inventors: Mark J. Bly, Falcon Heights, MN (US);
Badri Amurthur, Los Gatos, CA (US);
Kristofer J. James, Eagan, MN (US);
Imad Libbus, Saint Paul, MN (US);
Yatheendhar D. Manicka, Woodbury, MN (US); Scott T. Mazar, Woodbury, MN (US); Jerry S. Wang, Blaine, MN (US)

(73) Assignee: Corventis, Inc., San Jose, CA (US)

( * ) Notice: Subject to any disclaimer, the term of this patent is extended or adjusted under 35 U.S.C. 154(b) by 718 days.

(21) Appl. No.: 12/209,273

(22) Filed: Sep. 12, 2008

(65) Prior Publication Data

US 2009/0076363 A1    Mar. 19, 2009

Related U.S. Application Data

(60) Provisional application No. 60/972,537, filed on Sep. 14, 2007, provisional application No. 60/972,629, filed on Sep. 14, 2007, provisional application No. 61/055,666, filed on May 23, 2008, provisional application No. 61/055,645, filed on May 23, 2008.

(51) Int. Cl.
*A61B 5/04* (2006.01)
*A61B 5/0408* (2006.01)

(52) U.S. Cl. ........ 600/391; 600/382; 600/392; 600/393; 600/509; 600/301

(58) Field of Classification Search ............... 600/372, 600/382–386, 390–393, 529
See application file for complete search history.

(56) References Cited

U.S. PATENT DOCUMENTS

| 834,261 A | 10/1906 | Chambers |
| 2,087,124 A | 7/1937 | Smith et al. |

(Continued)

FOREIGN PATENT DOCUMENTS

AU    2003-220574 A8    10/2003

(Continued)

OTHER PUBLICATIONS

3M Corporation, "3M Surgical Tapes—Choose the Correct Tape" quicksheet (2004).*

(Continued)

*Primary Examiner* — Lee Cohen
*Assistant Examiner* — Erin M Cardinal
(74) *Attorney, Agent, or Firm* — Kilpatrick Townsend & Stockton, LLP

(57) ABSTRACT

An adherent device to monitor a patient for an extended period comprises a breathable tape. The breathable tape comprises a porous material with an adhesive coating to adhere the breathable tape to a skin of the patient. At least one electrode is affixed to the breathable tape and capable of electrically coupling to a skin of the patient. A printed circuit board is connected to the breathable tape to support the printed circuit board with the breathable tape when the tape is adhered to the patient. Electronic components electrically are connected to the printed circuit board and coupled to the at least one electrode to measure physiologic signals of the patient. A breathable cover and/or an electronics housing is disposed over the circuit board and electronic components and connected to at least one of the electronics components, the printed circuit board or the breathable tape.

40 Claims, 12 Drawing Sheets

U.S. PATENT DOCUMENTS

| | | | |
|---|---|---|---|
| 2,184,511 A | 12/1939 | Bagno et al. | |
| 3,170,459 A | 2/1965 | Phipps et al. | |
| 3,232,291 A | 2/1966 | Parker | |
| 3,370,459 A | 2/1968 | Cescati | |
| 3,517,999 A | 6/1970 | Weaver | |
| 3,620,216 A | 11/1971 | Szymanski | |
| 3,677,260 A | 7/1972 | Funfstuck et al. | |
| 3,805,769 A | 4/1974 | Sessions | |
| 3,845,757 A | 11/1974 | Weyer | |
| 3,874,368 A | 4/1975 | Asrican | |
| 3,882,853 A | 5/1975 | Gofman et al. | |
| 3,942,517 A | 3/1976 | Bowles et al. | |
| 3,972,329 A | 8/1976 | Kaufman | |
| 4,008,712 A | 2/1977 | Nyboer | |
| 4,024,312 A | 5/1977 | Korpman | |
| 4,077,406 A | 3/1978 | Sandhage et al. | |
| 4,121,573 A | 10/1978 | Crovella et al. | |
| 4,141,366 A | 2/1979 | Cross, Jr. et al. | |
| RE30,101 E | 9/1979 | Kubicek et al. | |
| 4,185,621 A | 1/1980 | Morrow | |
| 4,216,462 A | 8/1980 | McGrath et al. | |
| 4,300,575 A * | 11/1981 | Wilson | 607/152 |
| 4,308,872 A | 1/1982 | Watson et al. | |
| 4,358,678 A | 11/1982 | Lawrence | |
| 4,409,983 A | 10/1983 | Albert | |
| 4,450,527 A | 5/1984 | Sramek | |
| 4,451,254 A | 5/1984 | Dinius et al. | |
| 4,478,223 A | 10/1984 | Allor | |
| 4,498,479 A | 2/1985 | Martio et al. | |
| 4,522,211 A | 6/1985 | Bare et al. | |
| 4,661,103 A | 4/1987 | Harman | |
| 4,664,129 A | 5/1987 | Helzel et al. | |
| 4,669,480 A | 6/1987 | Hoffman | |
| 4,673,387 A | 6/1987 | Phillips et al. | |
| 4,681,118 A | 7/1987 | Asai et al. | |
| 4,692,685 A | 9/1987 | Blaze | |
| 4,699,146 A | 10/1987 | Sieverding | |
| 4,721,110 A | 1/1988 | Lampadius | |
| 4,730,611 A | 3/1988 | Lamb | |
| 4,781,200 A | 11/1988 | Baker | |
| 4,793,362 A | 12/1988 | Tedner | |
| 4,838,273 A | 6/1989 | Cartmell | |
| 4,838,279 A | 6/1989 | Fore | |
| 4,850,370 A | 7/1989 | Dower | |
| 4,880,004 A | 11/1989 | Baker, Jr. et al. | |
| 4,895,163 A | 1/1990 | Libke et al. | |
| 4,911,175 A | 3/1990 | Shizgal | |
| 4,945,916 A | 8/1990 | Kretschmer et al. | |
| 4,955,381 A | 9/1990 | Way et al. | |
| 4,966,158 A | 10/1990 | Honma et al. | |
| 4,981,139 A | 1/1991 | Pfohl | |
| 4,988,335 A | 1/1991 | Prindle et al. | |
| 4,989,612 A | 2/1991 | Fore | |
| 5,001,632 A | 3/1991 | Hall-Tipping | |
| 5,012,810 A | 5/1991 | Strand et al. | |
| 5,025,791 A | 6/1991 | Niwa | |
| 5,027,824 A | 7/1991 | Dougherty et al. | |
| 5,050,612 A | 9/1991 | Matsumura | |
| 5,063,937 A | 11/1991 | Ezenwa et al. | |
| 5,080,099 A | 1/1992 | Way et al. | |
| 5,083,563 A | 1/1992 | Collins | |
| 5,086,781 A | 2/1992 | Bookspan | |
| 5,113,869 A | 5/1992 | Nappholz et al. | |
| 5,125,412 A | 6/1992 | Thornton | |
| 5,133,355 A | 7/1992 | Strand et al. | |
| 5,140,985 A | 8/1992 | Schroeder et al. | |
| 5,150,708 A | 9/1992 | Brooks | |
| 5,168,874 A | 12/1992 | Segalowitz | |
| 5,226,417 A | 7/1993 | Swedlow et al. | |
| 5,241,300 A | 8/1993 | Buschmann | |
| 5,257,627 A | 11/1993 | Rapoport | |
| 5,271,411 A | 12/1993 | Ripley et al. | |
| 5,273,532 A | 12/1993 | Niezink et al. | |
| 5,282,840 A | 2/1994 | Hudrlik | |
| 5,291,013 A | 3/1994 | Nafarrate et al. | |
| 5,297,556 A | 3/1994 | Shankar | |
| 5,301,677 A | 4/1994 | Hsung | |
| 5,319,363 A | 6/1994 | Welch et al. | |
| 5,331,966 A | 7/1994 | Bennett et al. | |
| 5,335,664 A | 8/1994 | Nagashima | |
| 5,343,869 A | 9/1994 | Pross et al. | |
| 5,353,793 A | 10/1994 | Bornn | |
| 5,362,069 A | 11/1994 | Hall-Tipping | |
| 5,375,604 A | 12/1994 | Kelly et al. | |
| 5,411,530 A | 5/1995 | Akhtar | |
| 5,437,285 A | 8/1995 | Verrier et al. | |
| 5,443,073 A | 8/1995 | Wang et al. | |
| 5,449,000 A | 9/1995 | Libke et al. | |
| 5,450,845 A | 9/1995 | Axelgaard | |
| 5,454,377 A | 10/1995 | Dzwonczyk et al. | |
| 5,464,012 A | 11/1995 | Falcone | |
| 5,469,859 A | 11/1995 | Tsoglin et al. | |
| 5,482,036 A | 1/1996 | Diab et al. | |
| 5,503,157 A | 4/1996 | Sramek | |
| 5,511,548 A * | 4/1996 | Riazzi et al. | 600/391 |
| 5,511,553 A | 4/1996 | Segalowitz | |
| 5,518,001 A | 5/1996 | Snell | |
| 5,523,742 A | 6/1996 | Simkins et al. | |
| 5,529,072 A | 6/1996 | Sramek | |
| 5,544,661 A | 8/1996 | Davis et al. | |
| 5,558,638 A | 9/1996 | Evers et al. | |
| 5,560,368 A | 10/1996 | Berger | |
| 5,564,429 A | 10/1996 | Bornn et al. | |
| 5,564,434 A | 10/1996 | Halperin et al. | |
| 5,566,671 A | 10/1996 | Lyons | |
| 5,575,284 A | 11/1996 | Athan et al. | |
| 5,607,454 A | 3/1997 | Cameron et al. | |
| 5,632,272 A | 5/1997 | Diab et al. | |
| 5,634,468 A | 6/1997 | Platt et al. | |
| 5,642,734 A | 7/1997 | Ruben et al. | |
| 5,673,704 A | 10/1997 | Marchlinski et al. | |
| 5,678,562 A | 10/1997 | Sellers | |
| 5,687,717 A | 11/1997 | Halpern et al. | |
| 5,718,234 A | 2/1998 | Warden et al. | |
| 5,724,025 A | 3/1998 | Tavori | |
| 5,738,107 A | 4/1998 | Martinsen et al. | |
| 5,748,103 A | 5/1998 | Flach et al. | |
| 5,767,791 A | 6/1998 | Stoop et al. | |
| 5,769,793 A | 6/1998 | Pincus et al. | |
| 5,772,508 A | 6/1998 | Sugita et al. | |
| 5,772,586 A | 6/1998 | Heinonen et al. | |
| 5,778,882 A | 7/1998 | Raymond et al. | |
| 5,788,643 A | 8/1998 | Feldman | |
| 5,803,915 A | 9/1998 | Kremenchugsky et al. | |
| 5,807,272 A | 9/1998 | Kun | |
| 5,814,079 A | 9/1998 | Kieval | |
| 5,817,035 A | 10/1998 | Sullivan | |
| 5,833,603 A | 11/1998 | Kovacs et al. | |
| 5,836,990 A | 11/1998 | Li | |
| 5,855,614 A | 1/1999 | Stevens et al. | |
| 5,860,860 A | 1/1999 | Clayman | |
| 5,862,802 A | 1/1999 | Bird | |
| 5,862,803 A | 1/1999 | Besson et al. | |
| 5,865,733 A | 2/1999 | Malinouskas et al. | |
| 5,876,353 A | 3/1999 | Riff | |
| 5,904,708 A | 5/1999 | Goedeke | |
| 5,935,079 A | 8/1999 | Swanson et al. | |
| 5,941,831 A | 8/1999 | Turcott | |
| 5,944,659 A | 8/1999 | Flach et al. | |
| 5,949,636 A | 9/1999 | Johnson et al. | |
| 5,957,854 A | 9/1999 | Besson et al. | |
| 5,957,861 A | 9/1999 | Combs et al. | |
| 5,964,703 A | 10/1999 | Goodman et al. | |
| 5,970,986 A | 10/1999 | Bolz et al. | |
| 5,984,102 A | 11/1999 | Tay | |
| 5,987,352 A | 11/1999 | Klein et al. | |
| 6,007,532 A | 12/1999 | Netherly | |
| 6,027,523 A | 2/2000 | Schmieding | |
| 6,045,513 A | 4/2000 | Stone et al. | |
| 6,047,203 A | 4/2000 | Sackner et al. | |
| 6,047,259 A | 4/2000 | Campbell et al. | |
| 6,049,730 A | 4/2000 | Kristbjarnarson | |
| 6,050,267 A | 4/2000 | Nardella et al. | |
| 6,050,951 A | 4/2000 | Friedman et al. | |
| 6,052,615 A | 4/2000 | Feild et al. | |
| 6,067,467 A | 5/2000 | John | |
| 6,080,106 A | 6/2000 | Lloyd et al. | |

| | | | | | | |
|---|---|---|---|---|---|---|
| 6,081,735 | A | 6/2000 | Diab et al. | 6,600,949 B1 | 7/2003 | Turcott |
| 6,095,991 | A | 8/2000 | Krausman et al. | 6,602,201 B1 | 8/2003 | Hepp et al. |
| 6,102,856 | A | 8/2000 | Groff et al. | 6,605,038 B1 | 8/2003 | Teller et al. |
| 6,104,949 | A | 8/2000 | Pitts Crick et al. | 6,611,705 B2 | 8/2003 | Hopman et al. |
| 6,112,224 | A | 8/2000 | Peifer et al. | 6,616,606 B1 | 9/2003 | Petersen et al. |
| 6,117,077 | A * | 9/2000 | Del Mar et al. ............ 600/301 | 6,622,042 B1 | 9/2003 | Thacker |
| 6,125,297 | A | 9/2000 | Siconolfi | 6,636,754 B1 | 10/2003 | Baura et al. |
| 6,129,744 | A | 10/2000 | Boute | 6,641,542 B2 | 11/2003 | Cho et al. |
| 6,141,575 | A | 10/2000 | Price | 6,645,153 B2 | 11/2003 | Kroll et al. |
| 6,144,878 | A | 11/2000 | Schroeppel et al. | 6,649,829 B2 | 11/2003 | Garber et al. |
| 6,164,284 | A | 12/2000 | Schulman et al. | 6,650,917 B2 | 11/2003 | Diab et al. |
| 6,181,963 | B1 * | 1/2001 | Chin et al. ............ 604/20 | 6,658,300 B2 | 12/2003 | Govari et al. |
| 6,185,452 | B1 | 2/2001 | Schulman et al. | 6,659,947 B1 | 12/2003 | Carter et al. |
| 6,190,313 | B1 | 2/2001 | Hinkle | 6,659,949 B1 | 12/2003 | Lang et al. |
| 6,190,324 | B1 | 2/2001 | Kieval et al. | 6,687,540 B2 | 2/2004 | Marcovecchio |
| 6,198,394 | B1 | 3/2001 | Jacobsen et al. | 6,697,658 B2 | 2/2004 | Al-Ali |
| 6,198,955 | B1 | 3/2001 | Axelgaard et al. | RE38,476 E | 3/2004 | Diab et al. |
| 6,208,894 | B1 | 3/2001 | Schulman et al. | 6,699,200 B2 | 3/2004 | Cao et al. |
| 6,212,427 | B1 | 4/2001 | Hoover | 6,701,271 B2 | 3/2004 | Willner et al. |
| 6,213,942 | B1 | 4/2001 | Flach et al. | 6,714,813 B2 | 3/2004 | Ishigooka et al. |
| 6,225,901 | B1 | 5/2001 | Kail, IV | RE38,492 E | 4/2004 | Diab et al. |
| 6,245,021 | B1 | 6/2001 | Stampfer | 6,721,594 B2 | 4/2004 | Conley et al. |
| 6,259,939 | B1 | 7/2001 | Rogel | 6,728,572 B2 | 4/2004 | Hsu et al. |
| 6,272,377 | B1 | 8/2001 | Sweeney et al. | 6,748,269 B2 | 6/2004 | Thompson et al. |
| 6,277,078 | B1 | 8/2001 | Porat et al. | 6,749,566 B2 | 6/2004 | Russ |
| 6,287,252 | B1 | 9/2001 | Lugo | 6,751,498 B1 | 6/2004 | Greenberg et al. |
| 6,289,238 | B1 | 9/2001 | Besson et al. | 6,760,617 B2 | 7/2004 | Ward et al. |
| 6,290,646 | B1 | 9/2001 | Cosentino et al. | 6,773,396 B2 | 8/2004 | Flach et al. |
| 6,295,466 | B1 | 9/2001 | Ishikawa et al. | 6,775,566 B2 | 8/2004 | Nissila |
| 6,305,943 | B1 | 10/2001 | Pougatchev et al. | 6,790,178 B1 | 9/2004 | Mault et al. |
| 6,306,088 | B1 | 10/2001 | Krausman et al. | 6,795,722 B2 | 9/2004 | Sheraton et al. |
| 6,308,094 | B1 | 10/2001 | Shusterman et al. | 6,814,706 B2 | 11/2004 | Barton et al. |
| 6,312,378 | B1 | 11/2001 | Bardy | 6,816,744 B2 | 11/2004 | Garfield et al. |
| 6,315,721 | B2 | 11/2001 | Schulman et al. | 6,821,249 B2 | 11/2004 | Casscells, III et al. |
| 6,327,487 | B1 | 12/2001 | Stratbucker | 6,824,515 B2 | 11/2004 | Suorsa et al. |
| 6,336,903 | B1 | 1/2002 | Bardy | 6,827,690 B2 | 12/2004 | Bardy |
| 6,339,722 | B1 | 1/2002 | Heethaar et al. | 6,829,503 B2 | 12/2004 | Alt |
| 6,343,140 | B1 | 1/2002 | Brooks | 6,858,006 B2 | 2/2005 | MacCarter et al. |
| 6,347,245 | B1 | 2/2002 | Lee et al. | 6,871,211 B2 | 3/2005 | Labounty et al. |
| 6,358,208 | B1 | 3/2002 | Lang et al. | 6,878,121 B2 | 4/2005 | Krausman et al. |
| 6,385,473 | B1 | 5/2002 | Haines et al. | 6,879,850 B2 | 4/2005 | Kimball |
| 6,398,727 | B1 | 6/2002 | Bui et al. | 6,881,191 B2 | 4/2005 | Oakley et al. |
| 6,400,982 | B2 | 6/2002 | Sweeney et al. | 6,887,201 B2 | 5/2005 | Bardy |
| 6,411,853 | B1 | 6/2002 | Millot et al. | 6,890,096 B2 | 5/2005 | Tokita et al. |
| 6,416,471 | B1 | 7/2002 | Kumar et al. | 6,893,396 B2 | 5/2005 | Schulze et al. |
| 6,442,422 | B1 | 8/2002 | Duckert | 6,894,204 B2 | 5/2005 | Dunshee |
| 6,450,820 | B1 | 9/2002 | Palsson et al. | 6,906,530 B2 | 6/2005 | Geisel |
| 6,450,953 | B1 | 9/2002 | Place et al. | 6,912,414 B2 | 6/2005 | Tong |
| 6,454,707 | B1 | 9/2002 | Casscells, III et al. | 6,936,006 B2 | 8/2005 | Sabra |
| 6,454,708 | B1 | 9/2002 | Ferguson et al. | 6,940,403 B2 | 9/2005 | Kail, IV |
| 6,459,930 | B1 | 10/2002 | Takehara et al. | 6,942,622 B1 | 9/2005 | Turcott |
| 6,463,328 | B1 | 10/2002 | John | 6,952,695 B1 | 10/2005 | Trinks et al. |
| 6,473,640 | B1 | 10/2002 | Erlebacher | 6,970,742 B2 | 11/2005 | Mann et al. |
| 6,480,733 | B1 | 11/2002 | Turcott | 6,972,683 B2 | 12/2005 | Lestienne et al. |
| 6,480,734 | B1 | 11/2002 | Zhang et al. | 6,978,177 B1 | 12/2005 | Chen et al. |
| 6,490,478 | B1 | 12/2002 | Zhang et al. | 6,980,851 B2 | 12/2005 | Zhu et al. |
| 6,491,647 | B1 | 12/2002 | Bridger et al. | 6,980,852 B2 | 12/2005 | Jersey-Willuhn et al. |
| 6,494,829 | B1 | 12/2002 | New, Jr. et al. | 6,985,078 B2 | 1/2006 | Suzuki et al. |
| 6,496,715 | B1 | 12/2002 | Lee et al. | 6,987,965 B2 | 1/2006 | Ng et al. |
| 6,512,949 | B1 | 1/2003 | Combs et al. | 6,988,989 B2 | 1/2006 | Weiner et al. |
| 6,520,967 | B1 | 2/2003 | Cauthen | 6,993,378 B2 | 1/2006 | Wiederhold et al. |
| 6,527,711 | B1 | 3/2003 | Stivoric et al. | 6,997,879 B1 | 2/2006 | Turcott |
| 6,527,729 | B1 | 3/2003 | Turcott | 7,003,346 B2 | 2/2006 | Singer |
| 6,544,173 | B2 | 4/2003 | West et al. | 7,018,338 B2 | 3/2006 | Vetter et al. |
| 6,544,174 | B2 | 4/2003 | West et al. | 7,020,508 B2 | 3/2006 | Stivoric et al. |
| 6,551,251 | B2 | 4/2003 | Zuckerwar et al. | 7,027,862 B2 | 4/2006 | Dahl et al. |
| 6,551,252 | B2 | 4/2003 | Sackner et al. | 7,041,062 B2 | 5/2006 | Friedrichs et al. |
| 6,569,160 | B1 | 5/2003 | Goldin et al. | 7,044,911 B2 | 5/2006 | Drinan et al. |
| 6,572,557 | B2 | 6/2003 | Tchou et al. | 7,047,067 B2 | 5/2006 | Gray et al. |
| 6,572,636 | B1 | 6/2003 | Hagen et al. | 7,050,846 B2 | 5/2006 | Sweeney et al. |
| 6,577,139 | B2 | 6/2003 | Cooper | 7,054,679 B2 | 5/2006 | Hirsh |
| 6,577,893 | B1 | 6/2003 | Besson et al. | 7,059,767 B2 | 6/2006 | Tokita et al. |
| 6,579,231 | B1 | 6/2003 | Phipps | 7,088,242 B2 | 8/2006 | Aupperle et al. |
| 6,580,942 | B1 | 6/2003 | Willshire | 7,113,826 B2 | 9/2006 | Henry et al. |
| 6,584,343 | B1 | 6/2003 | Ransbury et al. | 7,118,531 B2 | 10/2006 | Krill |
| 6,587,715 | B2 | 7/2003 | Singer | 7,127,370 B2 | 10/2006 | Kelly, Jr. et al. |
| 6,589,170 | B1 | 7/2003 | Flach et al. | 7,129,836 B2 | 10/2006 | Lawson et al. |
| 6,595,927 | B2 | 7/2003 | Pitts-Crick et al. | 7,130,396 B2 | 10/2006 | Rogers et al. |
| 6,595,929 | B2 | 7/2003 | Stivoric et al. | 7,130,679 B2 | 10/2006 | Parsonnet et al. |

| Patent/Publication | Date | Inventor |
|---|---|---|
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy |
| 7,160,252 B2 | 1/2007 | Cho et al. |
| 7,160,253 B2 | 1/2007 | Nissila |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 | 4/2007 | Tarler |
| 7,212,849 B2 | 5/2007 | Zhang et al. |
| 7,215,984 B2 | 5/2007 | Diab et al. |
| 7,215,991 B2 | 5/2007 | Besson et al. |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,318,808 B2 | 1/2008 | Tarassenko et al. |
| 7,319,386 B2 | 1/2008 | Collins, Jr. et al. |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,384,398 B2 | 6/2008 | Gagnadre et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 7,701,227 B2 | 4/2010 | Saulnier et al. |
| 2001/0047127 A1 | 11/2001 | New, Jr. et al. |
| 2002/0019588 A1 | 2/2002 | Marro et al. |
| 2002/0028989 A1 | 3/2002 | Pelletier et al. |
| 2002/0032581 A1 | 3/2002 | Reitberg |
| 2002/0045836 A1 | 4/2002 | Alkawwas |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2003/0009092 A1 | 1/2003 | Parker |
| 2003/0023184 A1 | 1/2003 | Pitts-Crick et al. |
| 2003/0028221 A1 | 2/2003 | Zhu et al. |
| 2003/0028327 A1 | 2/2003 | Brunner et al. |
| 2003/0051144 A1 | 3/2003 | Williams |
| 2003/0055460 A1 | 3/2003 | Owens et al. |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0105411 A1 | 6/2003 | Smallwood et al. |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0010303 A1 | 1/2004 | Bolea et al. |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0073094 A1 | 4/2004 | Baker |
| 2004/0073126 A1 | 4/2004 | Rowlandson |
| 2004/0077954 A1 | 4/2004 | Oakley et al. |
| 2004/0100376 A1 | 5/2004 | Lye et al. |
| 2004/0102683 A1 | 5/2004 | Khanuja et al. |
| 2004/0106951 A1 | 6/2004 | Edman et al. |
| 2004/0127790 A1 | 7/2004 | Lang et al. |
| 2004/0133079 A1 | 7/2004 | Mazar et al. |
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0215247 A1 | 10/2004 | Bolz |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0059867 A1 | 3/2005 | Chung |
| 2005/0065445 A1 | 3/2005 | Arzbaecher et al. |
| 2005/0065571 A1 | 3/2005 | Imran |
| 2005/0070768 A1 | 3/2005 | Zhu et al. |
| 2005/0070778 A1 | 3/2005 | Lackey et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1 | 5/2005 | Ozguz et al. |
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |
| 2005/0137464 A1 | 6/2005 | Bomba |
| 2005/0137626 A1 | 6/2005 | Pastore et al. |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203436 A1 | 9/2005 | Davies |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228238 A1 | 10/2005 | Monitzer |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251044 A1 | 11/2005 | Hoctor et al. |
| 2005/0256418 A1 | 11/2005 | Mietus et al. |
| 2005/0261598 A1 | 11/2005 | Banet et al. |

| Publication No. | Date | Inventor |
|---|---|---|
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0273023 A1 | 12/2005 | Bystrom et al. |
| 2005/0277841 A1 | 12/2005 | Shennib |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0094948 A1 | 5/2006 | Gough et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0135858 A1 | 6/2006 | Nidd et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155183 A1 | 7/2006 | Kroecker et al. |
| 2006/0155200 A1 | 7/2006 | Ng |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |
| 2006/0224051 A1 | 10/2006 | Teller et al. |
| 2006/0224072 A1 | 10/2006 | Shennib |
| 2006/0224079 A1 | 10/2006 | Washchuk |
| 2006/0235281 A1 | 10/2006 | Tuccillo |
| 2006/0235316 A1 | 10/2006 | Ungless et al. |
| 2006/0235489 A1 | 10/2006 | Drew et al. |
| 2006/0241641 A1 | 10/2006 | Albans et al. |
| 2006/0241701 A1 | 10/2006 | Markowitz et al. |
| 2006/0241722 A1 | 10/2006 | Thacker et al. |
| 2006/0247545 A1 | 11/2006 | St. Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010721 A1 | 1/2007 | Chen et al. |
| 2007/0010750 A1 | 1/2007 | Ueno et al. |
| 2007/0015973 A1 | 1/2007 | Nanikashvili |
| 2007/0015976 A1 | 1/2007 | Miesel et al. |
| 2007/0016089 A1 | 1/2007 | Fischell et al. |
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0043303 A1 | 2/2007 | Osypka et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0082189 A1* | 4/2007 | Gillette ............ 428/304.4 |
| 2007/0083092 A1 | 4/2007 | Rippo et al. |
| 2007/0092862 A1 | 4/2007 | Gerber |
| 2007/0104840 A1 | 5/2007 | Singer |
| 2007/0106132 A1 | 5/2007 | Elhag et al. |
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1 | 6/2007 | Kwok et al. |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150008 A1 | 6/2007 | Jones et al. |
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0232867 A1 | 10/2007 | Hansmann |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0273504 A1 | 11/2007 | Tran |
| 2007/0276273 A1 | 11/2007 | Watson, Jr. |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004904 A1 | 1/2008 | Tran |

| | | | |
|---|---|---|---|
| 2008/0024293 A1 | 1/2008 | Stylos | |
| 2008/0024294 A1 | 1/2008 | Mazar | |
| 2008/0039700 A1 | 2/2008 | Drinan et al. | |
| 2008/0120784 A1 | 2/2008 | Warner et al. | |
| 2008/0058614 A1 | 3/2008 | Banet et al. | |
| 2008/0059239 A1 | 3/2008 | Gerst et al. | |
| 2008/0091089 A1 | 4/2008 | Guillory et al. | |
| 2008/0114220 A1 | 5/2008 | Banet et al. | |
| 2008/0139934 A1 | 6/2008 | McMorrow et al. | |
| 2008/0146892 A1 | 6/2008 | LeBoeuf et al. | |
| 2008/0167538 A1 | 7/2008 | Teller et al. | |
| 2008/0171918 A1 | 7/2008 | Teller et al. | |
| 2008/0171922 A1 | 7/2008 | Teller et al. | |
| 2008/0171929 A1 | 7/2008 | Katims | |
| 2008/0183052 A1 | 7/2008 | Teller et al. | |
| 2008/0200774 A1 | 8/2008 | Luo | |
| 2008/0214903 A1 | 9/2008 | Orbach | |
| 2008/0220865 A1 | 9/2008 | Hsu | |
| 2008/0221399 A1 | 9/2008 | Zhou et al. | |
| 2008/0221402 A1 | 9/2008 | Despotis | |
| 2008/0224852 A1 | 9/2008 | Dicks et al. | |
| 2008/0228084 A1 | 9/2008 | Bedard et al. | |
| 2008/0275465 A1 | 11/2008 | Paul et al. | |
| 2008/0287751 A1 | 11/2008 | Stivoric et al. | |
| 2008/0287752 A1 | 11/2008 | Stroetz et al. | |
| 2008/0293491 A1 | 11/2008 | Wu et al. | |
| 2008/0294019 A1 | 11/2008 | Tran | |
| 2008/0294020 A1 | 11/2008 | Sapounas | |
| 2008/0318681 A1 | 12/2008 | Rofougaran et al. | |
| 2008/0319279 A1 | 12/2008 | Ramsay et al. | |
| 2008/0319282 A1 | 12/2008 | Tran | |
| 2008/0319290 A1 | 12/2008 | Mao et al. | |
| 2009/0005016 A1 | 1/2009 | Eng et al. | |
| 2009/0018410 A1 | 1/2009 | Coene et al. | |
| 2009/0018456 A1 | 1/2009 | Hung | |
| 2009/0048526 A1 | 2/2009 | Aarts | |
| 2009/0054737 A1 | 2/2009 | Magar et al. | |
| 2009/0062670 A1 | 3/2009 | Sterling et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076364 A1 | 3/2009 | Libbus et al. | |
| 2009/0076397 A1 | 3/2009 | Libbus et al. | |
| 2009/0076401 A1 | 3/2009 | Mazar et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0182204 A1 | 7/2009 | Semler et al. | |
| 2009/0234410 A1 | 9/2009 | Libbus et al. | |
| 2009/0292194 A1 | 11/2009 | Libbus et al. | |
| 2010/0056881 A1 | 3/2010 | Libbus et al. | |
| 2010/0191310 A1 | 7/2010 | Bly et al. | |
| 2011/0144470 A1 | 6/2011 | Mazar et al. | |

FOREIGN PATENT DOCUMENTS

| | | |
|---|---|---|
| EP | 1487535 | 12/2004 |
| EP | 1579801 A1 | 9/2005 |
| JP | 2005-521448 | 7/2005 |
| WO | WO 00/79255 | 12/2000 |
| WO | WO 01/89362 A2 | 11/2001 |
| WO | WO 02/092101 | 11/2002 |
| WO | WO 03/082080 | 10/2003 |
| WO | WO 2005/051164 | 6/2005 |
| WO | WO 2005/104930 | 11/2005 |
| WO | WO 2006/008745 | 1/2006 |
| WO | WO 2006/102476 | 9/2006 |
| WO | WO 2006/111878 A1 | 11/2006 |
| WO | WO 2007/041783 | 4/2007 |
| WO | WO 2007/106455 A2 | 9/2007 |

OTHER PUBLICATIONS

AD5934: 250 kSPS 12-Bit Impedance Converter Network Analyzer, Analog Devices, retrieved from the Internet: <<http://www.analog.com/static/imported-files/data_sheets/AD5934.pdf>>, 40 pages.

Something in the way he moves, The Economist, 2007, retrieved from the Internet: <<http://www.economist.com/science/printerFriendly.cfm?story id=9861412>>.

Abraham, "New approaches to monitoring heart failure before symptoms appear," Rev Cardiovasc Med. 2006 ;7 Suppl 1 :33-41.

Adams, Jr. "Guiding heart failure care by invasive hemodynamic measurements: possible or useful?", Journal of Cardiac Failure 2002; 8(2):71-73.

Adamson et al., "Continuous autonomic assessment in patients with symptomatic heart failure: prognostic value of heart rate variability measured by an implanted cardiac resynchronization device ," Circulation. 2004;110:2389-2394.

Adamson et al., "Ongoing right ventricular hemodynamics in heart failure," J Am Coll Cardiol, 2003; 41:565-57.

Adamson, "Integrating device monitoring into the infrastructure and workflow of routine practice," Rev Cardiovasc Med. 2006 ;7 Suppl 1:42-6.

Adhere [presentation], "Insights from the Adhere Registry: Data from over 100,000 patient cases," 70 pages total.

Advamed White Sheet, "Health Information Technology: Improving Patient Safety and Quality of Care," Jun. 2005, 23 pages.

Aghababian, "Acutely decompensated heart failure: opportunities to improve care and outcomes in the emergency department," Rev Cardiovasc Med. 2002;3 Suppl 4:S3-9.

Albert, "Bioimpedance to prevent heart failure hospitalization," Curr Heart Fail Rep. Sep. 2006;3(3):136-42.

American Heart Association, "Heart Disease and Stroke Statistics-2006 Update," 2006, 43 pages.

American Heart Association, "Heart Disease and Stroke Statistics-2007 Update. A Report From the American Heart Association Statistics Committee and Stroke Statistics Subcommittee," Circulation 2007; 115;e69-e171.

Belalcazar et al., "Monitoring lung edema using the pacemaker pulse and skin electrodes," Physiol. Meas. 2005; 26:S153-S163.

Bennet, "Development of implantable devices for continuous ambulatory monitoring of central hemodynamic values in heart failure patients," PACE Jun. 2005; 28:573-584.

Bourge, "Case studies in advanced monitoring with the chronicle device," Rev Cardiovasc Med. 2006 ;7 Suppl 1:S56-61.

Braunschweig, "Continous haemodynamic monitoring during withdrawal of diuretics in patients with congestive heart failure," European Heart Journal 2002 23(1):59-69.

Braunschweig, "Dynamic changes in right ventricular pressures during haemodialysis recorded with an implantable haemodynamic monitor ," Nephrol Dial Transplant 2006; 21:176-183.

Brennan, "Measuring a Grounded Impedance Profile Using the AD5933," Analog Devices, retrieved from the internet <<http://http://www.analog.com/static/imported-files/application_notes/427095282381510189AN847_0.pdf>>, 12 pages total.

Buono et al., "The effect of ambient air temperature on whole-body bioelectrical impedance," Physiol. Meas. 2004;25:119-123.

Burkhoff et al., "Heart failure with a normal ejection fraction: Is it really a disorder of diastolic function?" Circulation 2003; 107:656-658.

Burr et al., "Heart rate variability and 24-hour minimum heart rate," Biological Research for Nursing, 2006; 7(4):256-267.

Cardionet, "CardioNet Mobile Cardiac Outpatient Telemetry: Addendum to Patient Education Guide", CardioNet, Inc., 2007, 2 pages.

Cardionet, "Patient Education Guide", CardioNet, Inc., 2007, 7 pages. Undated.

Charach et al., "Transthoracic monitoring of the impedance of the right lung in patients with cardiogenic pulmonary edema," Crit Care Med Jun. 2001;29(6):1137-1144.

Charlson et al., "Can disease management target patients most likely to generate high costs? The Impact of Comorbidity," Journal of General Internal Medicine, Apr. 2007, 22(4):464-469.

Chaudhry et al., "Telemonitoring for patients with chronic heart failure: a systematic review," J Card Fail. Feb. 2007; 13(1): 56-62.

Chung et al., "White coat hypertension: Not so benign after all?," Journal of Human Hypertension (2003) 17, 807-809.

Cleland et al., "The EuroHeart Failure survey programme—a survey on the quality of care among patients with heart failure in Europe—Part 1: patient characteristics and diagnosis," European Heart Journal 2003 24(5):442-463.

Cowie et al., "Hospitalization of patients with heart failure. A population-based study," European Heart Journal 2002 23(11):877-885.

Dimri, Chapter 1: Fractals in geophysics and seimology: an introduction, *Fractal Behaviour of the Earth System*, Springer Berlin Heidelberg 2005, pp. 1-22. [Summary and 1st page Only].

El-Dawlatly et al., "Impedance cardiography: noninvasive assessment of hemodynamics and thoracic fluid content during bariatric surgery," Obesity Surgery, May 2005, 15(5):655-658.

Erdmann, "Editorials: The value of diuretics in chronic heart failure demonstrated by an implanted haemodynamic monitor," European Heart Journal 2002 23(1):7-9.

FDA—Medtronic Inc., Chronicle 9520B Implantable Hemodynamic Monitor Reference Manual, 2007, 112 pages.

FDA Executive Summary Memorandum, prepared for Mar. 1, 2007, meeting of the Circulatory Systems Devices Advisory Panel, P050032 Medtronic, Inc. Chronicle Implantable Hemodynamic Monitor (IHM) System, 23 pages. Retrieved from the Internet: <<http://www.fda.gov/ohrms/dockets/ac/07/briefing/2007-4284b1_02.pdf>>.

FDA Executive Summary, Medtronic Chronicle Implantable Hemodynamic Monitoring System P050032: Panel Package Sponsor Executive Summary; vol. 1, section 4: Executive Summary. 12 pages total. Retrieved from the Internet: <<http://www.fda.gov/OOHRMS/DOCKETS/AC/07/briefing/2007-4284b1_03.pdf>>.

FDA—Medtronic Chronicle Implantable Hemodynamic Monitoring System P050032: Panel Package Section 11: Chronicle IHM Summary of Safety and Effectiveness, 2007; retrieved from the Internet: <http://www.fda.gov/OHRMS/DOCKETS/AC/07/briefing/2007-4284b1_04.pdf>, 77 pages total.

FDA, Draft questions for Chronicle Advisory Panel Meeting, 3 pages. Retrieved from the Internet: <<http://www.fda.gov/ohrms/dockets/ac/07/questions/2007-4284q1_draft.pdf>>.

FDA, References for Mar. 1 Circulatory System Devices Panel, 1 page total. 2007. Retrieved from the Internet: <<http://www.fda.gov/OHRMS/DOCKETS/AC/07/briefing/2007-4284bib1_01.pdf>>.

FDA Panel Recommendation, "Chronicle Analysis," Mar. 1, 2007, 14 pages total.

Fonarow et al., "Risk stratification for in-hospital mortality in acutely decompensated heart failure: classification and regression tree analysis," JAMA. Feb. 2, 2005;293(5):572-580.

Fonarow, "How well are chronic heart failure patients being managed?", Rev Cardiovasc Med. 2006;7 Suppl 1:S3-11.

Fonarow, "Maximizing Heart Failure Care" [Powerpoint Presentation], downloaded from the Internet <<http://www.medreviews.com/media/MaxHFCore.ppt>>, 130 pages total.

Fonarow, "Proactive monitoring and management of the chronic heart failure patient," Rev Cardiovasc Med. 2006; 7 Suppl 1:S1-2.

Fonarow, "The Acute Decompensated Heart Failure National Registry (ADHERE): opportunities to improve care of patients hospitalized with acute decompensated heart failure," Rev Cardiovasc Med. 2003;4 Suppl 7:S21-S30.

Ganion et al., "Intrathoracic impedance to monitor heart failure status: a comparison of two methods in a chronic heart failure dog model," Congest Heart Fail. Jul.-Aug. 2005;11(4):177-81, 211.

Gass et al., "Critical pathways in the management of acute decompensated heart failure: A CME-Accredited monograph," Mount Sinai School of Medicine, 2004, 32 pages total.

Gheorghiade et al., "Congestion is an important diagnostic and therapeutic target in heart failure," Rev Cardiovasc Med. 2006 ;7 Suppl 1 :12-24.

Gilliam, III et al., "Changes in heart rate variability, quality of life, and activity in cardiac resynchronization therapy patients: results of the HF-HRV registry," Pacing and Clinical Electrophysiology, Jan. 18, 2007; 30(1): 56-64.

Gilliam, III et al., "Prognostic value of heart rate variability footprint and standard deviation of average 5-minute intrinsic R-R intervals for mortality in cardiac resynchronization therapy patients.," J Electrocardiol. Oct. 2007;40(4):336-42.

Gniadecka, "Localization of dermal edema in lipodermatosclerosis, lymphedema, and cardiac insufficiency high-frequency ultrasound examination of intradermal echogenicity," J Am Acad oDermatol, Jul. 1996; 35(1):37-41.

Goldberg et al., "Randomized trial of a daily electronic home monitoring system in patients with advanced heart failure: The Weight Monitoring in Heart Failure (WHARF) Trial," American Heart Journal, Oct. 2003; 416(4):705-712.

Grap et al., "Actigraphy in the Critically Ill: Correlation With Activity, Agitation, and Sedation," American Journal of Critical Care. 2005;14: 52-60.

Gudivaka et al., "Single- and multifrequency models for bioelectrical impedance analysis of body water compartments," J Appl Physiol, 1999;87(3):1087-1096.

Guyton et al., Unit V: The Body Fluids and Kidneys, Chapter 25: The Body Fluid Compartments: Extracellular and Intracellular Fluids; Interstitial Fluid and Edema, *Guyton & Hall Textbook of Medical Physiology* 11th Edition, Saunders 2005; pp. 291-306.

Hadase et al., "Very low frequency power of heart rate variability is a powerful predictor of clinical prognosis in patients with congestive heart Failure," Circ J 2004; 68(4):343-347.

Hallstrom et al., "Structural relationships between measures based on heart beat intervals: potential for improved risk assessment," IEEE Biomedical Engineering 2004, 51(8):1414-1420.

HFSA 2006 Comprehensive Heart Failure Practice Guideline—Executive Summary: HFSA 2006 Comprehensive Heart Failure Practice Guideline, Journal of Cardiac Failure 2006;12(1):10-e38.

HFSA 2006 Comprehensive Heart Failure Practice Guideline—Section 12: Evaluation and Management of Patients With Acute Decompensated Heart Failure, Journal of Cardiac Failure 2006;12(1):e86-e103.

HFSA 2006 Comprehensive Heart Failure Practice Guideline—Section 2: Conceptualization and Working Definition of Heart Failure, Journal of Cardiac Failure 2006;12(1):e10-e11.

HFSA 2006 Comprehensive Heart Failure Practice Guideline—Section 3: Prevention of Ventricular Remodeling Cardiac Dysfunction, and Heart Failure Overview, Journal of Cardiac Failure 2006;12(1):e12-e15.

HFSA 2006 Comprehensive Heart Failure Practice Guideline—Section 4: Evaluation of Patients for Ventricular Dysfunction and Heart Failure, Journal of Cardiac Failure 2006;12(1):e16-e25.

HFSA 2006 Comprehensive Heart Failure Practice Guideline—Section 8: Disease Management in Heart Failure Education and Counseling, Journal of Cardiac Failure 2006;12(1):e58-e68.

Hunt et al., "ACC/AHA 2005 Guideline Update for the Diagnosis and Management of Chronic Heart Failure in the Adult: A Report of the American College of Cardiology/American Heart Association Task Force on Practice Guidelines (Writing Committee to Update the 2001 Guidelines for the Evaluation and Management of Heart Failure): Developed in Collaboration With the American College of Chest Physicians and the International Society for Heart and Lung Transplantation: Endorsed by the Heart Rhythm Society," Circulation. 2005;112:e154-e235.

Hunt et al., ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure), Circulation. 2001;104:2996-3007.

Imhoff et al., "Noninvasive whole-body electrical bioimpedance cardiac output and invasive thermodilution cardiac output in high-risk surgical patients," Critical Care Medicine 2000; 28(8):2812-2818.

Jaeger et al., "Evidence for Increased Intrathoracic Fluid Volume in Man at High Altitude," J Appl Physiol 1979; 47(6): 670-676.

Jerant et al., "Reducing the cost of frequent hospital admissions for congestive heart failure: a randomized trial of a home telecare intervention," Medical Care 2001, 39(11):1234-1245.

Jaio et al., "Variance fractal dimension analysis of seismic refraction signals," WESCANEX 97: Communications, Power and Computing. IEEE Conference Proceedings., May 22-23, 1997, pp. 163-167 [Abstract Only].

Kasper et al., "A randomized trial of the efficacy of multidisciplinary care in heart failure outpatients at high risk of hospital readmission," J Am Coll Cardiol, 2002; 39:471-480.

Kaukinen, "Cardiac output measurement after coronary artery bypass grafting using bolus thermodilution, continuous thermodilution, and whole-body impedance cardiography," Journal of Cardiothoracic and Vascular Anesthesia 2003; 17(2):199-203.

Kawaguchi et al., "Combined ventricular systolic and arterial stiffening in patients with heart failure and preserved ejection fraction: implications for systolic and diastolic reserve limitations," Circulation. 2003;107:714-720.

Kawasaki et al., "Heart rate turbulence and clinical prognosis in hypertrophic cardiomyopathy and myocardial infarction," Circ J. Jul. 2003;67(7):601-604.

Kearney et al., "Predicting death due to progressive heart failure in patients with mild-to-moderate chronic heart failure," J Am Coll Cardiol, 2002; 40(10):1801-1808.

Kitzman et al., "Pathophysiological characterization of isolated diastolic heart failure in comparison to systolic heart failure," JAMA Nov. 2002; 288(17):2144-2150.

Kööbi et al., "Non-invasive measurement of cardiac output : whole-body impedance cardiography in simultaneous comparison with thermodilution and direct oxygen Fick methods," Intensive Care Medicine 1997; 23(11):1132-1137.

Koyama et al., "Evaluation of heart-rate turbulence as a new prognostic marker in patients with chronic heart failure," Circ J 2002; 66(10):902-907.

Krumholz et al., "Predictors of readmission among elderly survivors of admission with heart failure," American Heart Journal 2000; 139(1):72-77.

Kyle et al., "Bioelectrical Impedance Analysis—part I: review of principles and methods," Clin Nutr. Oct. 2004;23(5):1226-1243.

Kyle et al., "Bioelectrical Impedance Analysis—part II: utilization in clinical practice," Clin Nutr. Oct. 2004;23(5):1430-1453.

Lee et al., "Predicting mortality among patients hospitalized for heart failure: derivation and validation of a clinical model," JAMA 2003;290(19):2581-2587.

Leier "The Physical Examination in Heart Failure—Part I," Congest Heart Fail. Jan.-Feb. 2007;13(1):41-47.

LifeShirt® Model 200 Directions for Use, "Introduction", VivoMetrics, Inc. 9 page total.

Liu et al., "Fractal analysis with applications to seismological pattern recognition of underground nuclear explosions," Singal Processing, Sep. 2000, 80(9):1849-1861. [Abstract Only].

Lozano-Nieto, "Impedance ratio in bioelectrical impedance measurements for body fluid shift determination," Proceedings of the IEEE 24th Annual Northeast Bioengineering Conference, Apr. 9-10, 1998, pp. 24-25.

Lucreziotti et al., "Five-minute recording of heart rate variability in severe chronic heart failure : Correlates with right ventricular function and prognostic implications," American Heart Journal 2000; 139(6):1088-1095.

Lüthje et al., "Detection of heart failure decompensation using intrathoracic impedance monitoring by a triple-chamber implantable defibrillator," Heart Rhythm Sep. 2005;2(9):997-999.

Magalski et al., "Continuous ambulatory right heart pressure measurements with an implantable hemodynamic monitor: a multicenter, 12-Month Follow-up Study of Patients With Chronic Heart Failure," J Card Fail 2002, 8(2):63-70.

Mahlberg et al., "Actigraphy in agitated patients with dementia: Monitoring treatment outcomes," Zeitschrift für Gerontologie and Geriatrie, Jun. 2007; 40(3)178-184. [Abstract Only].

Matthie et al., "Analytic assessment of the various bioimpedance methods used to estimate body water," Appl Physiol 1998; 84(5):1801-1816.

Matthie, "Second generation mixture theory equation for estimating intracellular water using bioimpedance spectroscopy," J Appl Physiol 2005; 99:780-781.

McMurray et al., "Heart Failure: Epidemiology, Aetiology, and Prognosis of Heart Failure," Heart 2000;83:596-602.

Miller, "Home monitoring for congestive heart failure patients," Caring Magazine, Aug. 1995: 53-54.

Moser et al., "Improving outcomes in heart failure: it's not unusual beyond usual Care," Circulation. 2002;105:2810-2812.

Nagels et al., "Actigraphic measurement of agitated behaviour in dementia," International journal of geriatric psychiatry , 2009; 21(4):388-393. [Abstract Only].

Nakamura et al., "Universal scaling law in human behavioral organization," Physical Review Letters, Sep. 28, 2007; 99(13):138103 (4 pages).

Nakaya, "Fractal properties of seismicity in regions affected by large, shallow earthquakes in western Japan: Implications for fault formation processes based on a binary fractal fracture network model," Journal of geophysical research, Jan. 2005; 11(B1):B01310.1-B01310.15. [Abstract Only].

Naylor et al., "Comprehensive discharge planning for the hospitalized elderly: a randomized clinical trial ," Amer. College Physicians 1994; 120(12):999-1006.

Nesiritide (Natrecor) [Presentation] Acutely Decompensated Congestive Heart Failure: Burden of Disease, downloaded from the Internet: <<http://www.huntsvillehospital.org/foundation/events/cardiologyupdate/CHF.ppt.>>, 39 pages.

Nieminen et al., "EuroHeart Failure Survey II (EHFS II): a survey on hospitalized acute heart failure patients: description of population," European Heart Journal 2006; 27(22):2725-2736.

Nijsen et al., "The potential value of three-dimensional accelerometry for detection of motor seizures in severe epilepsy," Epilepsy Behav. Aug. 2005;7(1):74-84.

Noble et al., "Diuretic induced change in lung water assessed by electrical impedance tomography," Physiol. Meas. 2000; 21(1):155-163.

Noble et al., "Monitoring patients with left ventricular failure by electrical impedance tomography," Eur J Heart Fail. Dec. 1999;1(4):379-84.

O'Connell et al., "Economic impact of heart failure in the United States: time for a different approach," J Heart Lung Transplant., Jul.-Aug. 1994; 13(4):S107-S112.

Ohlsson et al., "Central hemodynamic responses during serial exercise tests in heart failure patients using implantable hemodynamic monitors," Eur J Heart Fail. Jun. 2003;5(3):253-259.

Ohlsson et al., "Continuous ambulatory monitoring of absolute right ventricular pressure and mixed venous oxygen saturation in patients with heart failure using an implantable haemodynamic monitor," European Heart Journal 2001 22(11):942-954.

Packer et al., "Utility of impedance cardiography for the identification of short-term risk of clinical decompensation in stable patients with chronic heart failure," J Am Coll Cardiol, 2006; 47(11):2245-2252.

Palatini et al., "Predictive value of clinic and ambulatory heart rate for mortality in elderly subjects with systolic hypertension" Arch Intern Med. 2002;162:2313-2321.

Piiria et al., "Crackles in patients with fibrosing alveolitis bronchiectasis, COPD, and Heart Failure," Chest May 1991; 99(5):1076-1083.

Pocock et al., "Predictors of mortality in patients with chronic heart failure," Eur Heart J 2006; (27): 65-75.

Poole-Wilson, "Importance of control of fluid volumes in heart failure," European Heart Journal 2000; 22(11):893-894.

Raj et al., 'Letter Regarding Article by Adamson et al, "Continuous Autonomic Assessment in Patients With Symptomatic Heart Failure: Prognostic Value of Heart Rate Variability Measured by an Implanted Cardiac Resynchronization Device"', Circulation 2005;112:e37-e38.

Ramirez et al., "Prognostic value of hemodynamic findings from impedance cardiography in hypertensive stroke," AJH 2005; 18(20):65-72.

Rich et al., "A multidisciplinary intervention to prevent the readmission of elderly patients with congestive heart failure," New Engl. J. Med. 1995;333:1190-1195.

Roglieri et al., "Disease management interventions to improve outcomes in congestive heart failure," Am J Manag Care. Dec. 1997;3(12):1831-1839.

Sahalos et al., "The Electrical impedance of the human thorax as a guide in evaluation of intrathoracic fluid volume," Phys. Med. Biol. 1986; 31:425-439.

Saxon et al., "Remote active monitoring in patients with heart failure (rapid-rf): design and rationale," Journal of Cardiac Failure 2007; 13(4):241-246.

Scharf et al., "Direct digital capture of pulse oximetry waveforms," Proceedings of the Twelfth Southern Biomedical Engineering Conference, 1993., pp. 230-232.

Shabetai, "Monitoring heart failure hemodynamics with an implanted device: its potential to improve outcome," J Am Coll Cardiol, 2003; 41:572-573.

Small, "Integrating monitoring into the Infrastructure and Workflow of Routine Practice: OptiVol," Rev Cardiovasc Med. 2006 ;7 Supp 1: S47-S55.

Smith et al., "Outcomes in heart failure patients with preserved ejection fraction: mortality, readmission, and functional decline ," J Am Coll Cardiol, 2003; 41:1510-1518.

Someren, "Actigraphic monitoring of movement and rest-activity rhythms inaging, Alzheimer's disease, and Parkinson's disease," IEEE Transactions on Rehabilitation Engineering, Dec. 1997; 5(4):394-398. [Abstract Only].

Starling, "Improving care of chronic heart failure: advances from drugs to devices," Cleveland Clinic Journal of Medicine Feb. 2003; 70(2):141-146.

Steijaert et al., "The use of multi-frequency impedance to determine total body water and extracellular water in obese and lean female individuals," International Journal of Obesity Oct. 1997; 21(10):930-934.

Stewart et al., "Effects of a home-based intervention among patients with congestive heart failure discharged from acute hospital care," Arch Intern Med. 1998;158:1067-1072.

Stewart et al., "Effects of a multidisciplinary, home-based intervention on planned readmissions and survival among patients with chronic congestive heart failure: a randomised controlled study," The Lancet Sep. 1999, 354(9184):1077-1083.

Stewart et al., "Home-based intervention in congestive heart failure: long-term implications on readmission and survival," Circulation. 2002;105:2861-2866.

Stewart et al., "Prolonged beneficial effects of a home-based intervention on unplanned readmissions and mortality among patients with congestive heart failure," Arch Intern Med. 1999;159:257-261.

Stewart et al., "Trends in Hospitalization for Heart Failure in Scotland, 1990-1996. An Epidemic that has Reached Its Peak?," European Heart Journal 2001 22(3):209-217.

Swedberg et al., "Guidelines for the diagnosis and treatment of chronic heart failure: executive summary (update 2005): The Task Force for the Diagnosis and Treatment of Chronic Heart Failure of the European Society of Cardiology," Eur Heart J. Jun. 2005; 26(11):1115-1140.

Tang, "Case studies in advanced monitoring: OptiVol," Rev Cardiovasc Med. 2006;7 Suppl 1:S62-S66.

The ESCAPE Investigators and ESCAPE Study Coordinators, "Evaluation Study of Congestive Heart Failure and Pulmonary Artery Catheterization Effectiveness," JAMA 2005;294:1625-1633.

Tosi et al., "Seismic signal detection by fractal dimension analysis ," Bulletin of the Seismological Society of America; Aug. 1999; 89(4):970-977. [Abstract Only].

Van De Water et al., "Monitoring the chest with impedance," Chest. 1973;64:597-603.

Vasan et al., "Congestive heart failure in subjects with normal versus reduced left ventricular ejection fraction," J Am Coll Cardiol, 1999; 33:1948-1955.

Verdecchia et al., "Adverse prognostic value of a blunted circadian rhythm of heart rate in essential hypertension," Journal of Hypertension 1998; 16(9):1335-1343.

Verdecchia et al., "Ambulatory pulse pressure: a potent predictor of total cardiovascular risk in hypertension," Hypertension. 1998;32:983-988.

Vollmann et al., "Clinical utility of intrathoracic impedance monitoring to alert patients with an implanted device of deteriorating chronic heart failure," Euorpean Heart Journal Advance Access published on Feb. 19, 2007, downloaded from the Internet:<<http://eurheartj.oxfordjournals.org/cgi/content/full/ehl506v1>>, 6 pages total.

Vuksanovic et al., "Effect of posture on heart rate variability spectral measures in children and young adults with heart disease," International Journal of Cardiology 2005;101(2): 273-278.

Wang et al., "Feasibility of using an implantable system to measure thoracic congestion in an ambulatory chronic heart failure canine model," PACE 2005;28(5):404-411.

Wickemeyer et al., #197—"Association between atrial and ventricular tachyarrhythmias, intrathoracic impedance and heart failure decompensation in CRT-D Patients," Journal of Cardiac Failure 2007; 13 (6) Suppl.; S131-132.

Williams et al, "How do different indicators of cardiac pump function impact upon the long-term prognosis of patients with chronic heart failure," American Heart Journal, 150(5):983.e1-983.e6.

Wonisch et al., "Continuous haemodynamic monitoring during exercise in patients with pulmonary hypertension," Int J Cardiol. Jun. 8, 2005;101(3):415-420.

Wynne et al., "Impedance cardiography: a potential monitor for hemodialysis," Journal of Surgical Research 2006, 133(1):55-60.

Yancy "Current approaches to monitoring and management of heart failure," Rev Cardiovasc Med 2006; 7 Suppl 1:S25-32.

Ypenburg et al., "Intrathoracic Impedance Monitoring to Predict Decompensated Heart Failure," Am J Cardiol 2007, 99(4):554-557.

Yu et al., "Intrathoracic Impedance Monitoring in Patients With Heart Failure: Correlation With Fluid Status and Feasibility of Early Warning Preceding Hospitalization," Circulation. 2005;112:841-848.

Zannad et al., "Incidence, clinical and etiologic features, and outcomes of advanced chronic heart failure: The EPICAL Study," J Am Coll Cardiol, 1999; 33(3):734-742.

Zile, "Heart failure with preserved ejection fraction: is this diastolic heart failure?" J Am Coll Cardiol, 2003; 41(9):1519-1522.

U.S. Appl. No. 60/006,600, filed Nov. 13, 1995; inventor: Terry E. Flach.

U.S. Appl. No. 60/972,316, filed Sep. 12, 2008; inventor: Imad Libbus et al.

U.S. Appl. No. 60/972,329, filed Sep. 14, 2007; inventor: Yatheendhar Manicka et al.

U.S. Appl. No. 60/972,333, filed Sep. 14, 2007; inventor: Mark Bly et al.

U.S. Appl. No. 60/972,336, filed Sep. 14, 2007; inventor: James Kristofer et al.

U.S. Appl. No. 60/972,340, filed Sep. 14, 2007; inventor: James Kristofer et al.

U.S. Appl. No. 60/972,343, filed Sep. 14, 2007; inventor: James Kristofer et al.

U.S. Appl. No. 60/972,354, filed Sep. 14, 2007; inventor: Scott Thomas Mazar et al.

U.S. Appl. No. 60/972,359, filed Sep. 14, 2007; inventor: Badri Amurthur et al.

U.S. Appl. No. 60/972,363, filed Sep. 14, 2007; inventor: Badri Amurthur et al.

U.S. Appl. No. 60/972,512, filed Sep. 14, 2007; inventor: Imad Libbus et al.

U.S. Appl. No. 60/972,537, filed Sep. 14, 2007; inventor: Yatheendhar Manicka et al.

U.S. Appl. No. 60/972,581, filed Sep. 14, 2007; inventor: Imad Libbus et al.

U.S. Appl. No. 60/972,616, filed Sep. 14, 2007; inventor: Imad Libbus et al.

U.S. Appl. No. 60/972,629, filed Sep. 14, 2007; inventor: Mark Bly et al.

U.S. Appl. No. 61/035,970, filed Mar. 12, 2008; inventor: Imad Libbus et al.

U.S. Appl. No. 61/046,196, filed Apr. 18, 2008; inventor: Scott T. Mazar.

U.S. Appl. No. 61/047,875, filed Apr. 25, 2008; inventor: Imad Libbus et al.

U.S. Appl. No. 61/055,645, filed May 23, 2008; inventor: Mark Bly et al.

U.S. Appl. No. 61/055,656, filed May 23, 2008; inventor: Imad Libbus et al.

U.S. Appl. No. 61/055,662, filed May 23, 2008; inventor: Imad Libbus et al.

U.S. Appl. No. 61/055,666, filed May 23, 2008; inventor: Yatheendhar Manicka et al.

U.S. Appl. No. 61/079,746, filed Jul. 10, 2008; inventor: Brett Landrum.

U.S. Appl. No. 61/084,567, filed Jul. 29, 2008; inventor: Mark Bly.

"Acute Decompensated Heart Failure"—Wikipedia Entry, downloaded from: <http://en.wikipedia.org/wiki/Acute_decompensated_heart_failure>, submitted version downloaded Feb. 11, 2011, 6 pages total.

"Heart Failure"—Wikipedia Entry, downloaded from the Internet: <http://en.wikipedia.org/wiki/Heart_failure>, submitted version downloaded Feb. 11, 2011, 17 pages total.

Cooley, "The Parameters of Transthoracic Electical Conduction," Annals of the New York Academy of Sciences, 1970; 170(2);702-713.

EM Microelectronic—Marin SA, "Platstic Flexible LCD," [product brochure]; retrieved from the Internet: <<http://www.em-microelectronic.com/Line.asp?IdLine=48>>, copyright 2009, 2 pages total.

HRV Enterprises, LLC, "Heart Rate Variability Seminars," downloaded from the Internet: <<http://hrventerprise.com/>> on Apr. 24, 2008, 3 pages total.

HRV Enterprises, LLC, "LoggerPro HRV Biosignal Analysis," downloaded from the Internet: <<http://hrventerprise.com/products.html>> on Apr. 24, 2008, 3 pages total.

* cited by examiner

FIG. 1D1

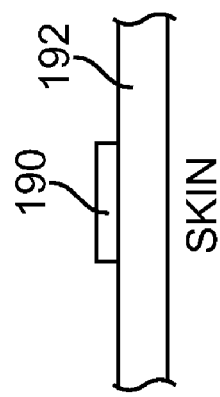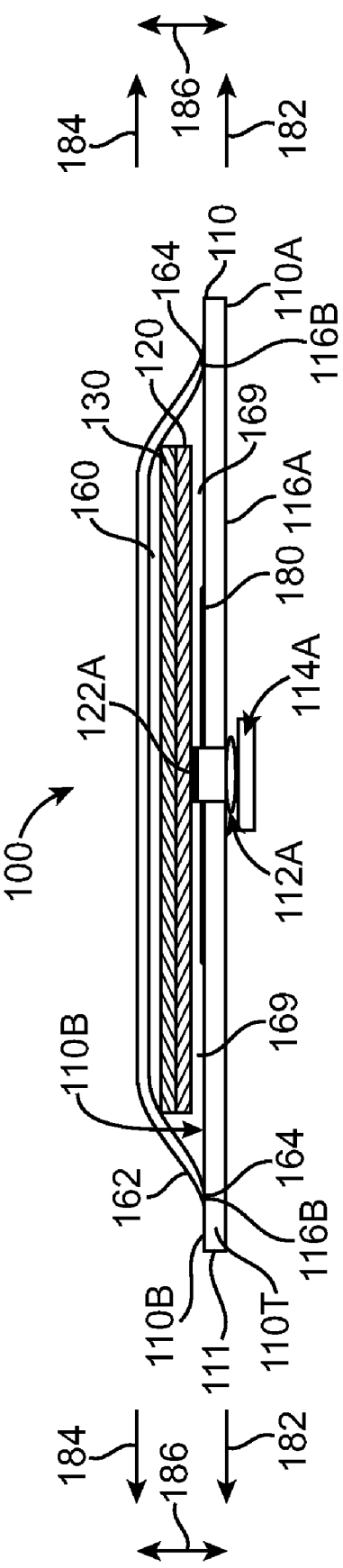

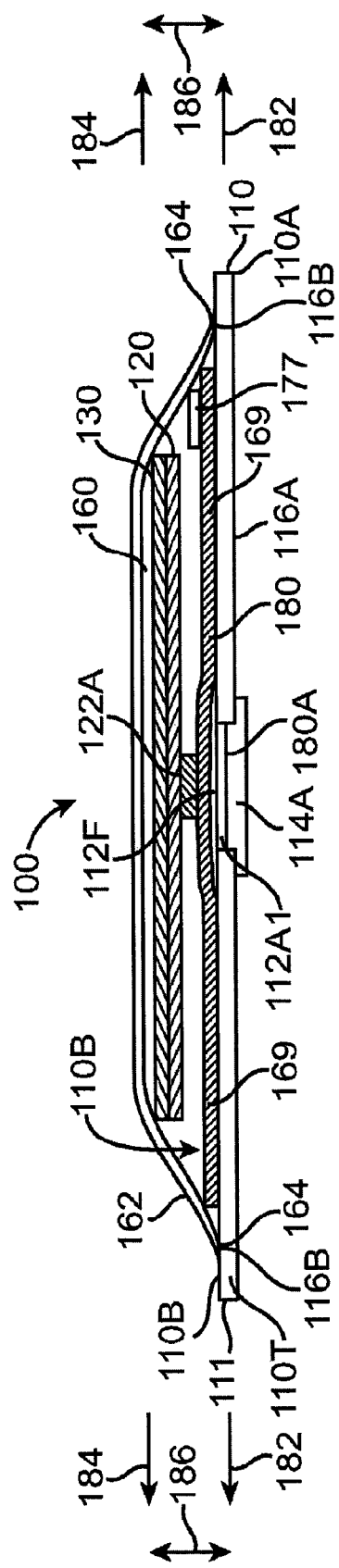
FIG. 1I1

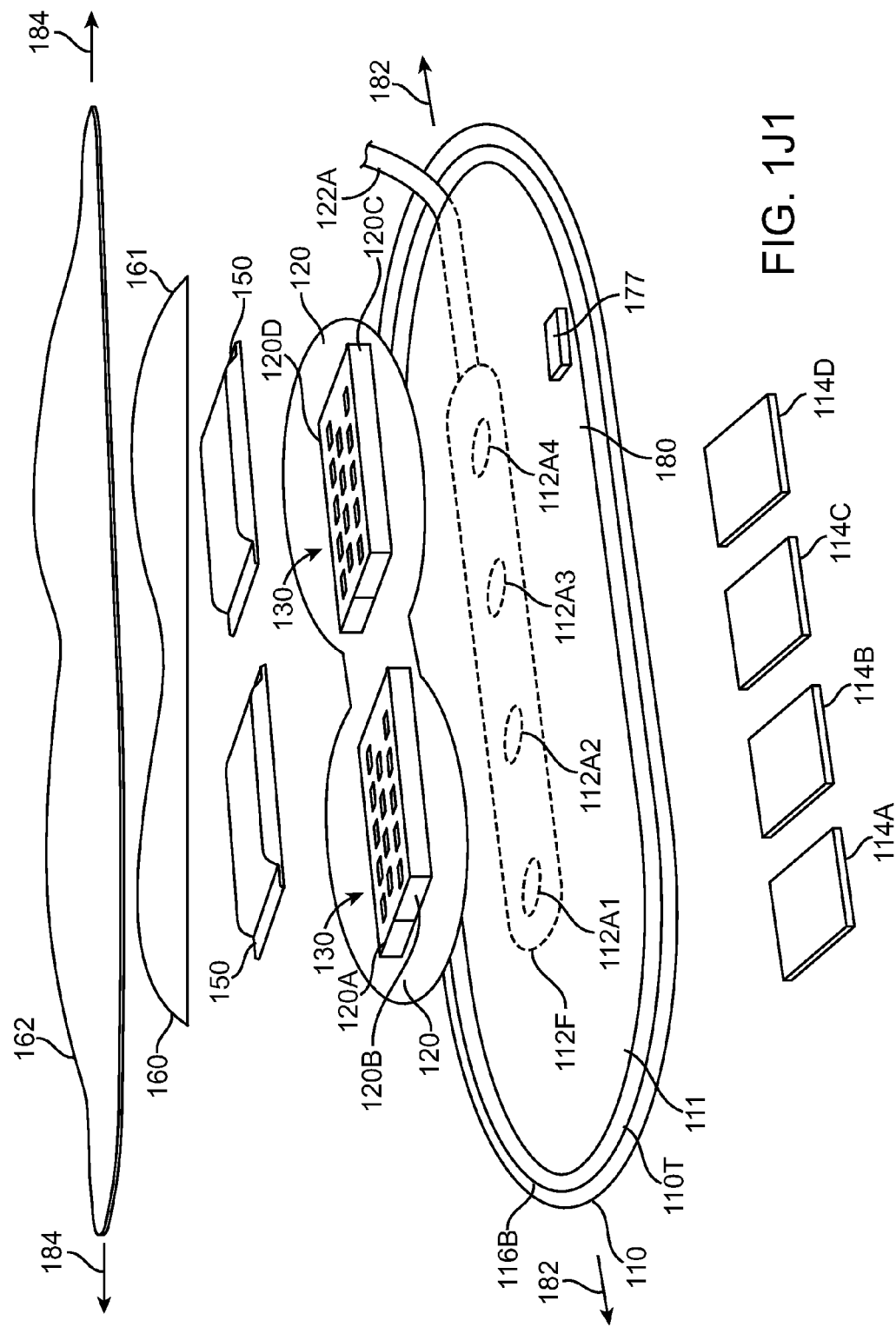

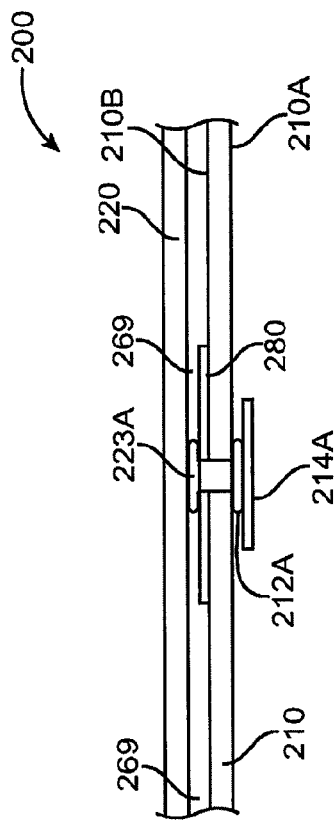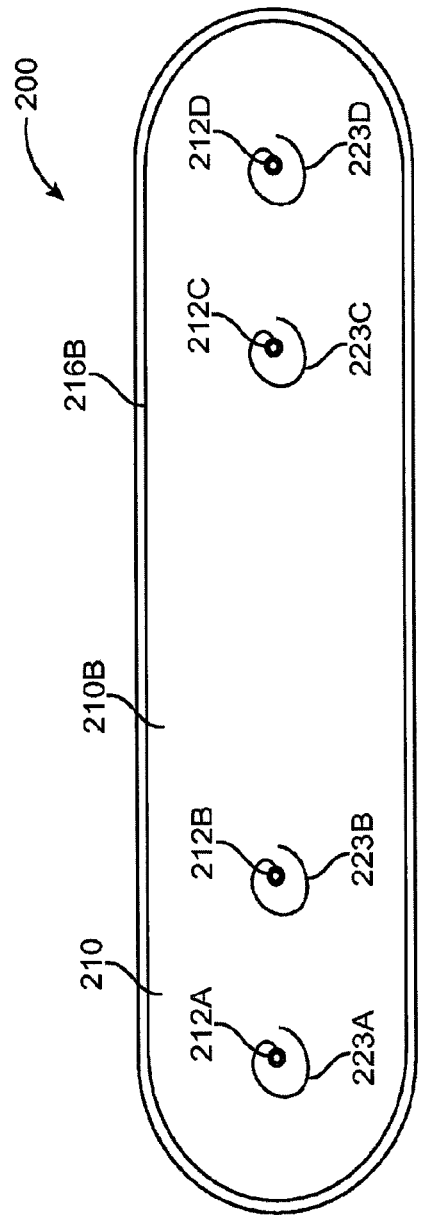

ADHERENT DEVICE WITH MULTIPLE PHYSIOLOGICAL SENSORS

CROSS-REFERENCES TO RELATED APPLICATIONS

The present application claims the benefit under 35 USC 119(e) of U.S. Provisional Application Nos. 60/972,629 and 60/972,537 both filed Sep. 14, 2007, and 61/055,645 and 61/055,666 both filed May 23, 2008; the full disclosures of which are incorporated herein by reference in their entirety.

The subject matter of the present application is related to the following applications: 60/972,512; 60/972,329; 60/972,354; 60/972,616; 60/972,363; 60/972,343; 60/972,581; 60/972,316; 60/972,333; 60/972,359; 60/972,336; 60/972,340 all of which were filed on Sep. 14, 2007; 61/046,196 filed Apr. 18, 2008; 61/047,875 filed Apr. 25, 2008; 61/055,656 and 61/055,662 both filed May 23, 2008; and 61/079,746 filed Jul. 10, 2008.

The following applications are being filed concurrently with the present application, on Sep. 12, 2008: Ser. No. 12/209,279 entitled "Multi-Sensor Patient Monitor to Detect Impending Cardiac Decompensation Prediction"; Ser. No. 12/209,288 entitled "Adherent Device with Multiple Physiological Sensors"; Ser. No. 12/209,430 entitled "Injectable Device for Physiological Monitoring"; Ser. No. 12/209,479 entitled "Delivery System for Injectable Physiological Monitoring System"; Ser. No. 12/209,262 entitled "Adherent Device for Cardiac Rhythm Management"; Ser. No. 12/209,268 entitled "Adherent Device for Respiratory Monitoring"; Ser. No. 12/209,269 entitled "Adherent Athletic Monitor"; Ser. No. 12/209,259 entitled "Adherent Emergency Monitor"; Ser. No. 12/209,276 entitled "Medical Device Automatic Start-up upon Contact to Patient Tissue"; Ser. No. 12/210,078 entitled "System and Methods for Wireless Body Fluid Monitoring"; Ser. No. 12/209,265 entitled "Adherent Cardiac Monitor with Advanced Sensing Capabilities"; Ser. No. 12/209,292 entitled "Adherent Device for Sleep Disordered Breathing"; Ser. No. 12/209,278 entitled "Dynamic Pairing of Patients to Data Collection Gateways"; Ser. No. 12/209,508 entitled "Adherent Multi-Sensor Device with Implantable Device Communications Capabilities"; Ser. No. 12/209,528 entitled "Data Collection in a Multi-Sensor Patient Monitor"; Ser. No. 12/209,271 entitled "Adherent Multi-Sensor Device with Empathic Monitoring"; Ser. No. 12/209,274 entitled "Energy Management for Adherent Patient Monitor"; and Ser. No. 12/209,294 entitled "Tracking and Security for Adherent Patient Monitor."

BACKGROUND OF THE INVENTION

1. Field of the Invention

The present invention relates to patient monitoring and/or therapy. Although embodiments make specific reference to monitoring impedance and electrocardiogram signals with an adherent device, the system methods and devices described herein may be applicable to many applications in which physiological monitoring and/or therapy is used for extended periods, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that are positioned across the midline of the patient, and may be somewhat uncomfortable and/or cumbersome for the patient to wear. In at least some instances, the electrodes that are held against the skin of the patient may become detached and/or dehydrated, such that the electrodes must be replaced, thereby making long term monitoring more difficult.

Work in relation to embodiments of the present invention suggests that known methods and apparatus for long term monitoring of patients may be less than ideal. In at least some instances, devices that are worn by the patient may be somewhat uncomfortable, which may lead to patients not wearing the devices and not complying with direction from the health care provider, such that data collected may be less than ideal.

Therefore, a need exists for improved patient monitoring. Ideally, such improved patient monitoring would avoid at least some of the short-comings of the present methods and devices.

2. Description of the Background Art

The following U.S. Patents and Publications may describe relevant background art: U.S. Pat. Nos. 3,170,459; 3,370,459; 3,805,769; 3,845,757; 3,972,329; 4,121,573; 4,141,366; 4,838,273; 4,955,381; 4,981,139; 5,080,099; 5,353,793; 5,511,553; 5,544,661; 5,558,638; 5,724,025; 5,772,586; 5,862,802; 6,047,203; 6,117,077; 6,129,744; 6,225,901; 6,385,473; 6,416,471; 6,454,707; 6,527,711; 6,527,729; 6,551,252; 6,595,927; 6,595,929; 6,605,038; 6,645,153; 6,795,722; 6,821,249; 6,980,851; 7,020,508; 7,054,679; 7,153,262; 2003/0092975; 2005/0113703; 2005/0131288; 2006/0010090; 2006/0031102; 2006/0089679; 2006/122474; 2006/0155183; 2006/0224051; 2006/0264730; 2007/0021678; and 2007/0038038.

BRIEF SUMMARY OF THE INVENTION

The present invention relates to patient monitoring. Although embodiments make specific reference to monitoring impedance and electrocardiogram signals with an adherent patch, the system methods and device described herein may be applicable to any application in which physiological monitoring and/or therapy is used for extended periods, for example wireless physiological monitoring for extended periods. In many embodiments, the adherent device comprises a breathable support, for example a breathable adherent patch, and breathable cover that can be used for extended periods with improved patient comfort. The breathable adherent patch, for example breathable tape, and breathable cover may be configured to stretch, for example to stretch together along two dimensions of the skin of the patient when the patch is adhered to the skin of the patient, such that patient comfort and the lifetime of the patch on the skin can be improved.

In a first aspect, embodiments of the present invention provide an adherent device to monitor a patient for an extended period. The device comprises a breathable tape. The breathable tape comprising a porous material with an adhesive coating to adhere the breathable tape to a skin of the patient. At least one electrode is affixed to the breathable tape and capable of electrically coupling to a skin of the patient. A printed circuit board is connected to the breathable tape to support the printed circuit board with the breathable tape when the tape is adhered to the patient. Electronic components are electrically connected to the printed circuit board and coupled to the at least one electrode to measure physiologic signals of the patient. At least one of a breathable cover or an electronics housing is disposed over the circuit board and electronic components and connected to at least one of the electronics components, the printed circuit board or the breathable tape.

In many embodiments, the printed circuit board is connected to the breathable tape with an intermediate connector, for example to provide strain relief and/or decouple motion of the tape from the printed circuit board so as to provide comfort for the patient.

In many embodiments, a gap extends between the breathable tape and the printed circuit board. The gap may extend between the breathable tape and printed circuit board for a distance from about 0.25 mm to about 4 mm to allow the tape to breath under the printed circuit board when the tape is adhered to the patient. The gap can allow the tape to adhered to the body to conform to the skin and not be restricted by structures supported with the tape, for example rigid structures such as the printed circuitry board.

In many embodiments, the breathable cover comprises a stretchable material. This stretchable material can allow the cover to move and/or stretch, for example with the breathable tape, in response to patient movement. In many embodiments, the stretchable material comprises at least one of polyester fabric, nylon or polyamide fabric and the stretchable material comprises from about 5 to 25% elastane fabric. The stretchable material may comprise at least about 100% elongation, for example an elastomeric material comprising at least about 400% elongation.

In many embodiments, the breathable cover comprises at least one of a water repellant outside coating to repel water or hydrophilic inside coating to wick moisture away from the skin of the patient. Although either coating can be effective to keep excess moisture from the gel over the electrodes and can remove moisture from the skin of the patient for comfort, for example through the breathable tape, both coatings may be used together. The breathable cover may comprise a fabric weight from about 100 to 200 grams per square meter.

In many embodiments, the device comprises a flexible connection structure to couple the electrodes to the printed circuit board so as to relieve strain between the electrodes and the printed circuit board. The printed circuit board may be adhered to the breathable tape at a central location and the breathable tape may be configured to stretch with the skin of the patient away from the central location. The flexible connection structure can support the printed circuit board with a gap between the printed circuit board and the breathable tape. The flexible connection structure may comprise at least one of shielded wires, non-shielded wires, a flexible printed circuit board, or polyester film with silver printing.

In many embodiments, the breathable tape comprises a flexible material and a thickness from about 0.005" to about 0.010". In specific embodiments, the breathable tape may comprise a backing, which comprises a polyester knit fabric and a thickness from about 0.005" to about 0.010".

In many embodiments, the breathable tape comprises an acrylate pressure sensitive adhesive on an under side of the tape, the adhesive having a thickness less than about 0.004" to allow the tape to breath when the adhesive is applied to the patient.

In many embodiments, the adherent device comprises an electronics housing adhered to at least one of the electronics components or the printed circuit board, such that the electronics housing is disposed between the cover and electronics components. The electronics housing may comprise a waterproof encapsulant to protect the printed circuit board and the electronic components from moisture and/or mechanical forces.

In many embodiments, the adherent device comprises a gel cover positioned over the breathable tape to inhibit a flow of the gel through the breathable tape, and the printed circuit board is located over the gel cover such that the gel cover is disposed between the breathable tape and the printed circuit board. In specific embodiments, the gel cover may comprise at least one of a polyurethane film or polyurethane non-woven backing and an acrylate pressure sensitive adhesive. The gel cover may comprise a porosity of at least about 200 sec./100 $cc/in^2$ to protect the hydrogel from external moisture. An edge of the gel cover may extend from about 5 to about 15 mm beyond an edge of a gel over the at least one electrode. In specific embodiments, the breathable tape may comprise a knit polyester fabric backing and the gel cover comprises a polyurethane, film backing.

In some embodiments, the breathable tape may comprise a first porosity, and the gel cover may comprise a breathable tape with a second porosity, the second porosity less than the first porosity to inhibit flow of the gel through the breathable tape having the first porosity.

In many embodiments, the breathable tape, the adhesive coating, the at least one electrode and the gel are separable from the printed circuit board, the electronic components and the at least one of the breathable cover or electronics housing, such that the printed circuit board, the electronic components, and the at least one of the breathable cover or the electronics housing are reusable.

In many embodiments, the at least one electrode extends through at least one aperture in the breathable tape. At least one gel can be disposed over a contact surface of the at least one electrode to electrically connect the electrode to the skin.

In some embodiments, the at least one electrode can be configured to electrically couple to the printed circuit board through the breathable tape.

In many embodiments, an adhesive can be disposed around the breathable tape to connect the cover to the breathable tape.

In many embodiments, the breathable tape comprises an MVTR of at least about 400 $g/m^2/24$ hrs. The adherent device may further comprise a gel cover positioned over the breathable tape and an MVTR through the breathable tape and the gel cover comprises at least about 400 $g/m^2/24$ hrs. An MVTR through the breathable tape, the gel cover and the breathable cover may comprise at least about 400 $g/m^2/24$ hrs.

In another aspect, embodiments of the present invention provide an adherent device to monitor and/or treat a patient. A breathable support comprises a porous material with an adhesive coating to adhere the breathable support to a skin of the patient. A breathable cover is disposed over the breathable support. At least one of the cover or the breathable support is configured to stretch with the skin of the patient.

In many embodiments, the breathable cover is configured to stretch with the breathable support.

In many embodiments, the breathable support comprises a breathable tape.

In another aspect, embodiments of the present invention provide an adherent device to monitor and/or treat a patient, The device comprises a means for adhering to the patient and a means for covering.

BRIEF DESCRIPTION OF THE DRAWINGS

FIG. 1D1 shows an equivalent circuit that can be used to determine optimal frequencies for determining patient hydration, according to embodiments of the present invention;

FIGS. 1I and 1J show a side cross-sectional view and an exploded view, respectively, of the adherent device as in FIGS. 1A to 1H;

FIGS. 1I1 and 1J1 show a side cross-sectional view and an exploded view, respectively, of an adherent device with a temperature sensor affixed to the gel cover, according to embodiments of the present invention;

FIG. 1K shows at least one electrode configured to electrically couple to a skin of the patient through a breathable tape, according to embodiments of the present invention; and FIGS. 2A and 2B show components of an adherent device comprising an adhesive patch and connection structures to provide strain relief so as to decouple the adhesive patch from an electronics module, according to embodiments of the present invention.

DETAILED DESCRIPTION OF THE INVENTION

Embodiments of the present invention relate to patient monitoring and/or therapy. Although embodiments make specific reference to monitoring impedance and electrocardiogram signals with an adherent device, the system methods and device described herein may be applicable to any application in which physiological monitoring and/or therapy is used for extended periods, for example wireless physiological monitoring for extended periods.

The adherent device comprises a support, for example a patch that may comprise breathable tape, and the support can be configured to adhere to the patient and support the electronics and sensors on the patient. The support can be porous and breathable so as to allow water vapor transmission. The support can also stretch with skin of the patient, so as to improve patient comfort and extend the time that the support can be adhered to the patient.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the patch can be worn and/or tolerated by the patient for extended periods, for example 90 days or more. The patch may be worn continuously for at least seven days, for example 14 days, and then replaced with another patch. Adherent devices with comfortable patches that can be worn for extended periods and in which patches can be replaced and the electronics modules reused are described in U.S. Pat. App. Nos. 60/972,537, entitled "Adherent Device with Multiple Physiological Sensors"; and 60/972,629, entitled "Adherent Device with Multiple Physiological Sensors", both filed on Sep. 14, 2007, the full disclosures of which have been previously incorporated herein by reference. In many embodiments, the adherent patch comprises a tape, which comprises a material, preferably breathable, with an adhesive, such that trauma to the patient skin can be minimized while the patch is worn for the extended period. The printed circuit board may comprise a flex printed circuit board that can flex with the patient to provide improved patient comfort.

Figure 1A:
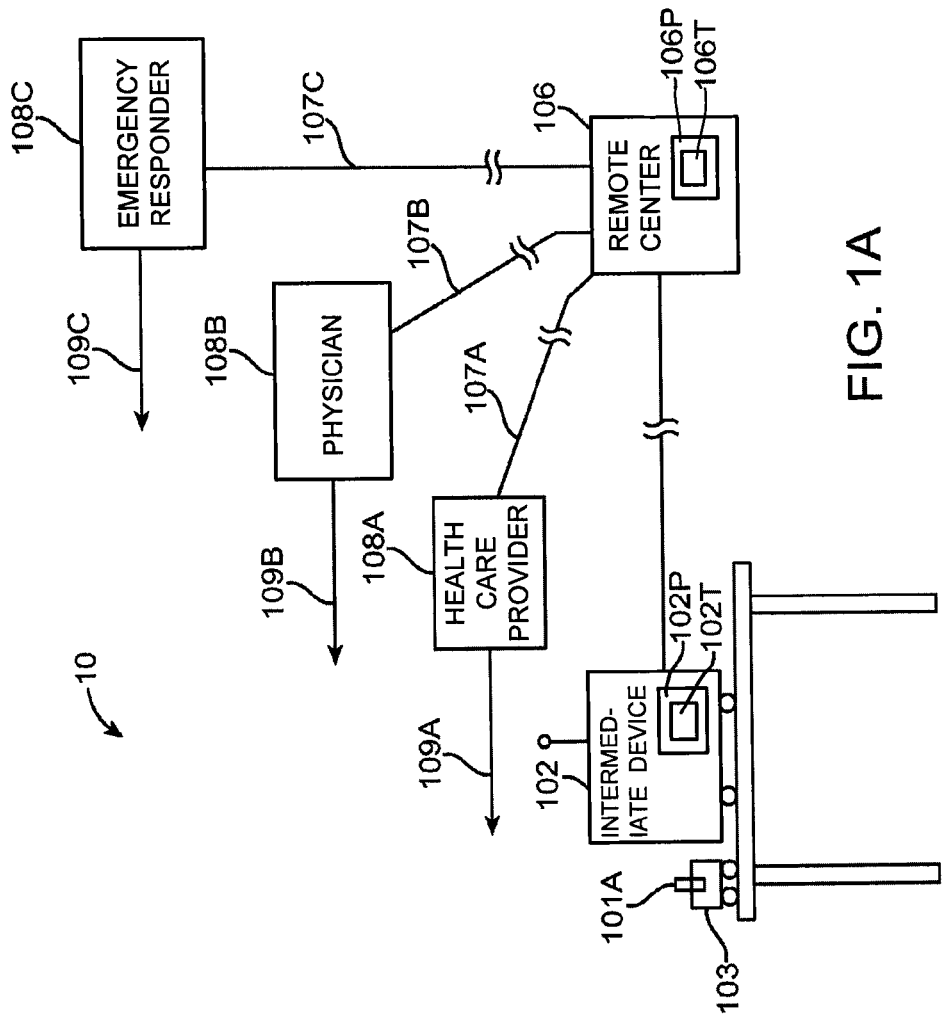
FIG. 1A shows a patient and a monitoring system comprising an adherent device, according to embodiments of the present invention.
Figure 1A:
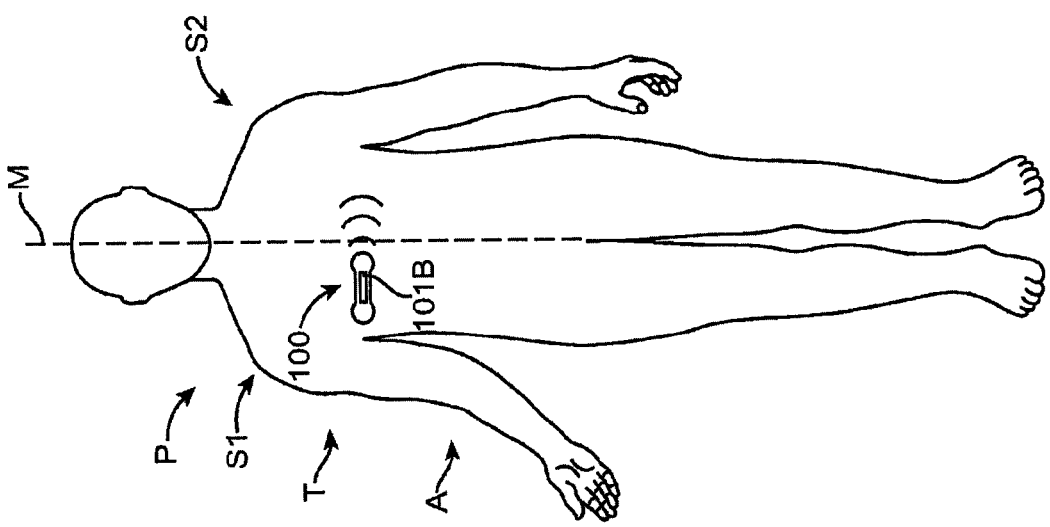

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Remote center 106 can be located in a different building from the patient, for example in the same town as the patient, and can be located as far from the patient as a separate continent from the patient, for example the patient located on a first continent and the remote center located on a second continent. Adherent device 100 can communicate wirelessly to an intermediate device 102, for example with a single wireless hop from the adherent device on the patient to the intermediate device. Intermediate device 102 can communicate with remote center 106 in many ways, for example with an internet connection and/or with a cellular connection. In many embodiments, monitoring system 10 comprises a distributed processing system with at least one processor comprising a tangible medium on device 100, at least one processor on intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C.

Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, the remote center 106 receives the patient data and applies a patient evaluation and/or prediction algorithm. When a flag is raised, the center may communicate with the patient, hospital, nurse, and/or physician to allow for therapeutic intervention, for example to prevent decompensation.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, hear rate variability (hereinafter "HRV"), heart rate turbulence (hereinafter "HRT"), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

Figure 1B:
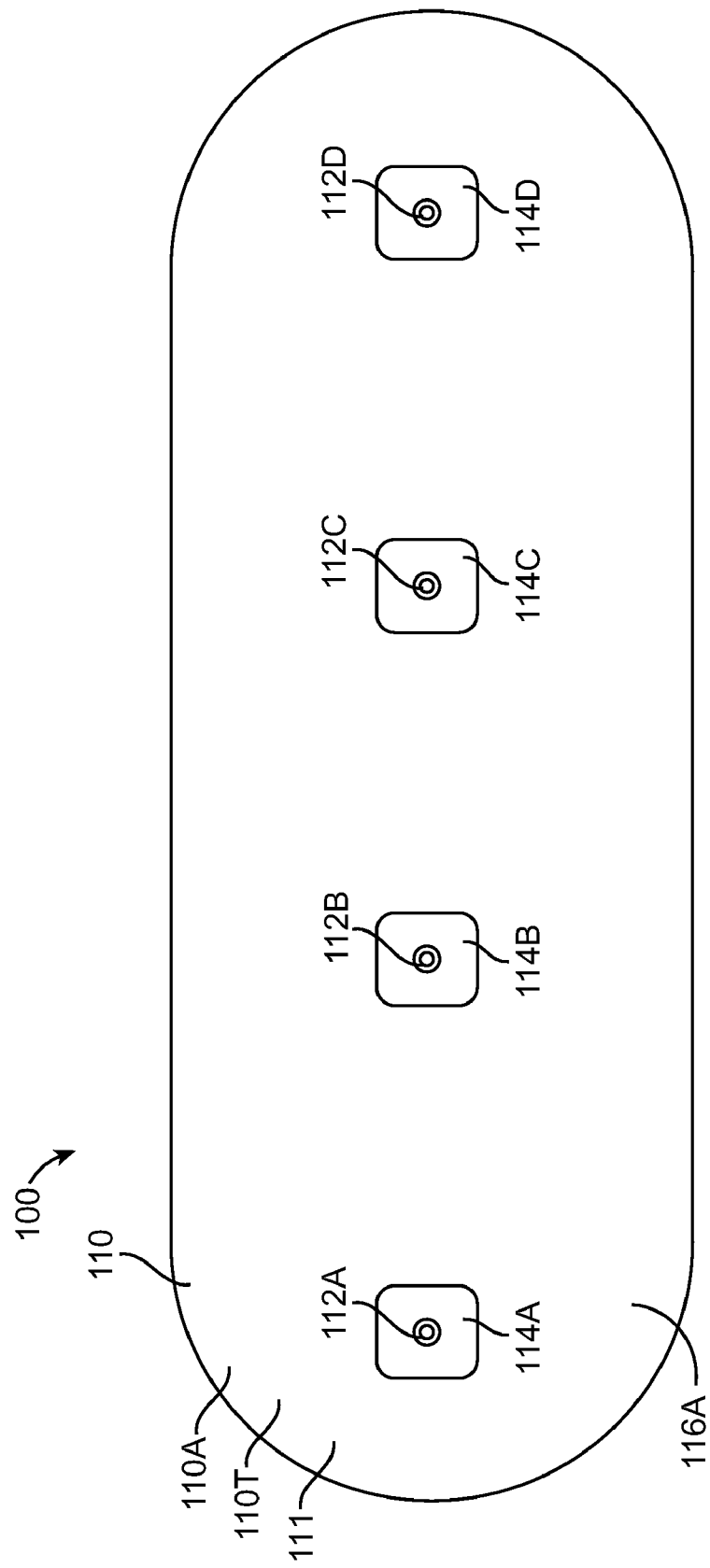
FIG. 1B shows a bottom view of the adherent device as in FIG. 1A comprising an adherent patch.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
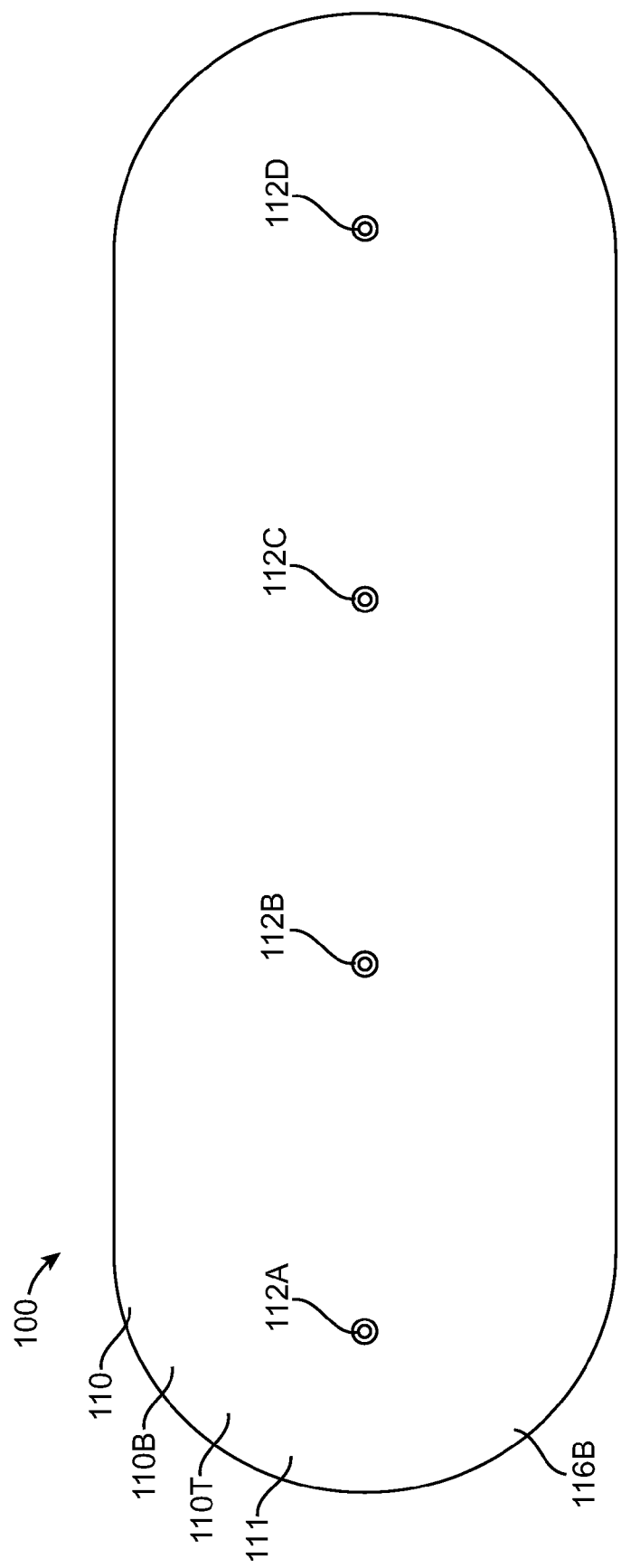
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The printed circuit board (hereinafter "PCB") may comprise completely flex PCB, combined flex PCB and/or rigid PCB boards connected by cable.

Figure 1D:
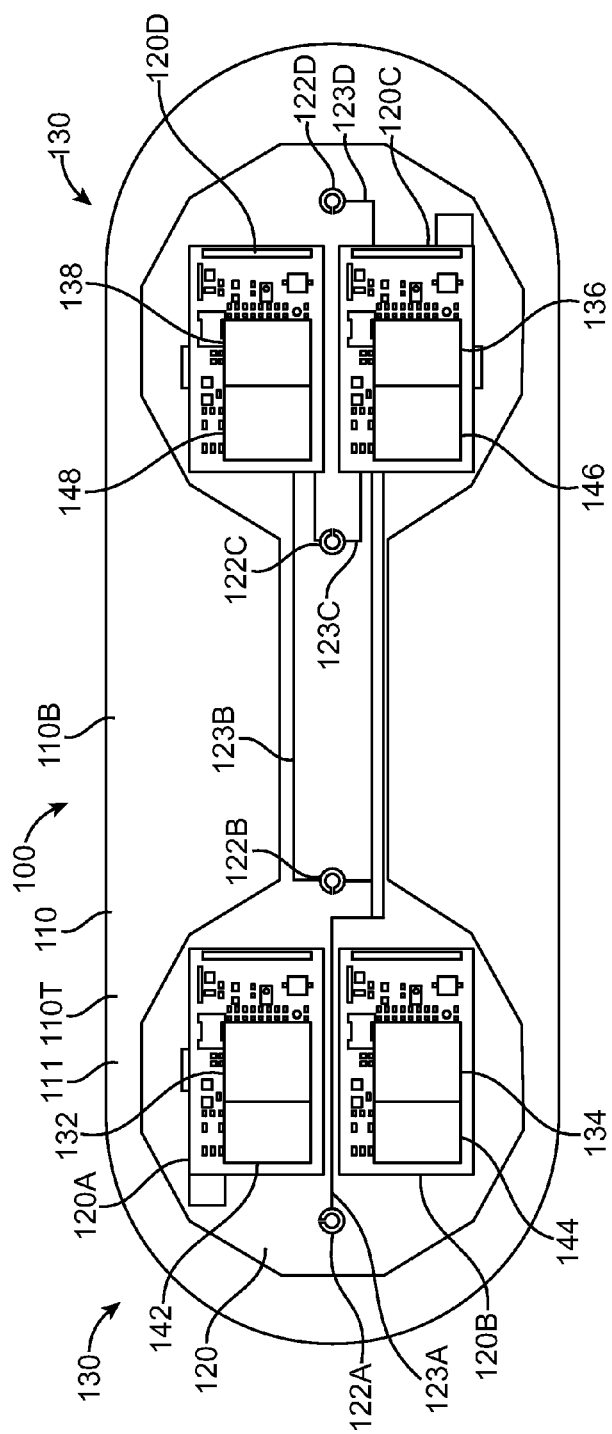
FIG. 1D shows a printed circuit boards and electronic components over the adherent patch, as in FIG. 1C.
Figure 1D:
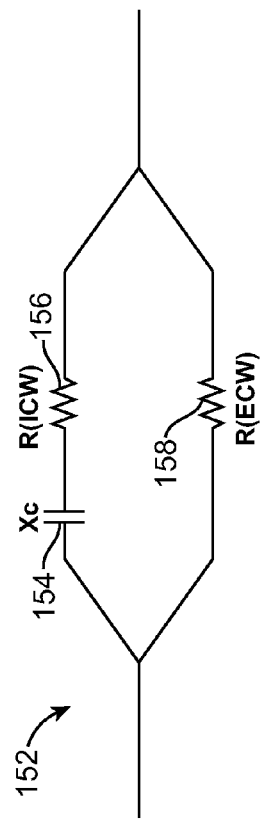

FIG. 1D shows a printed circuit boards and electronic components over adherent patch 110, as in FIGS. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex printed circuit board. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible film, such as at least one of known polyester film or known polyurethane film, coated with a conductive ink, for example a conductive silver ink. In some embodiments, additional PCB's, for example rigid PCB's 120A, 120B, 120C and 120D, can be connected to flex PCB 120. Electronic components 130 can be connected to flex PCB 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 138. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor 177, for example a thermistor in contact with the skin of the patient, and temperature sensor circuitry 144 to measure a temperature of the patient, for example a temperature of the skin of the patient. A temperature sensor 177 may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. Printed circuit board 120 may comprise an antenna to facilitate wireless communication. The antennae may be integral with printed circuit board 120 or may be separately coupled thereto. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data.

Impedance circuitry 136 can generate both hydration data and respiration data. In many embodiments, impedance circuitry 136 is electrically connected to electrodes 112A, 112B, 112C and 112D such that electrodes 112A and 112D comprise outer electrodes that are driven with a current, or force electrodes. The current delivered between electrodes 112A and 112D generates a measurable voltage between electrodes 112B and 112C, such that electrodes 112B and 112C comprise inner sense electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used measure the impedance of the patient to determine respiration rate and/or the hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention employ measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

Figure 1E:
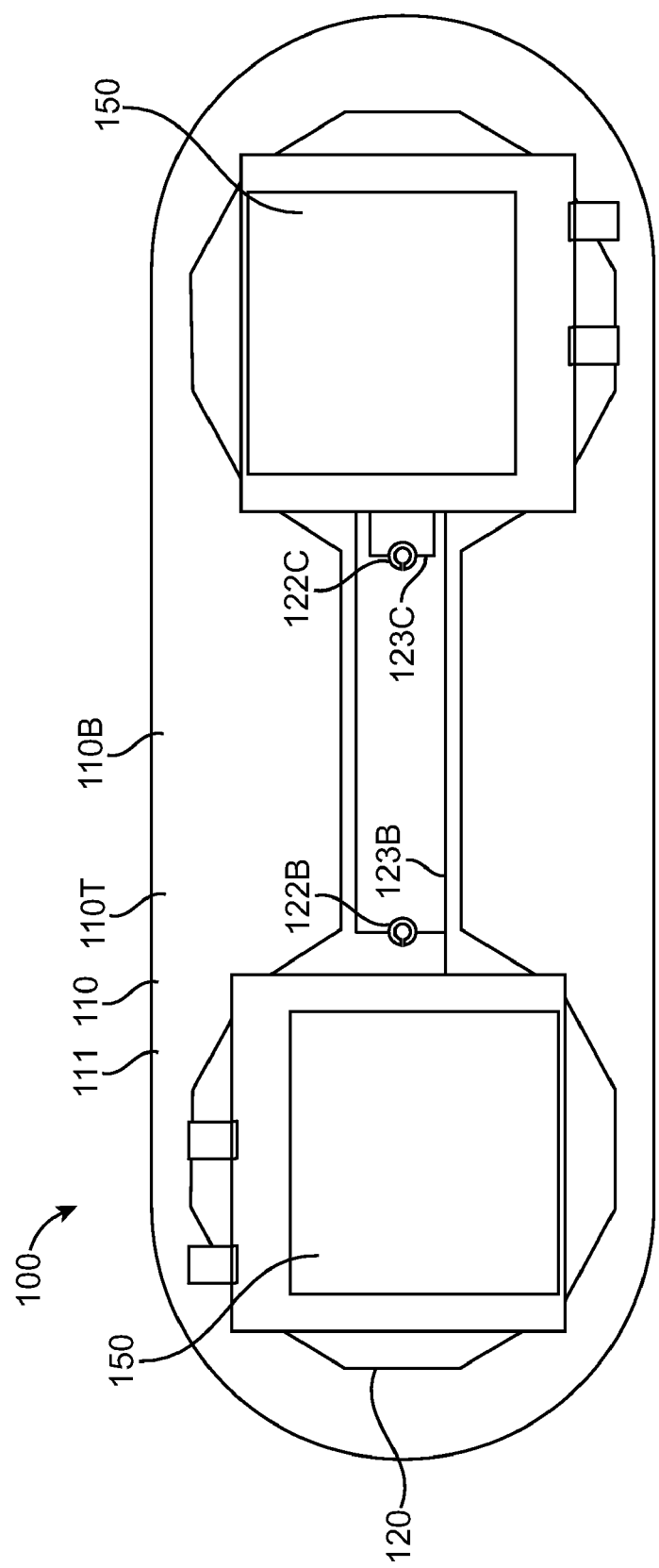
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
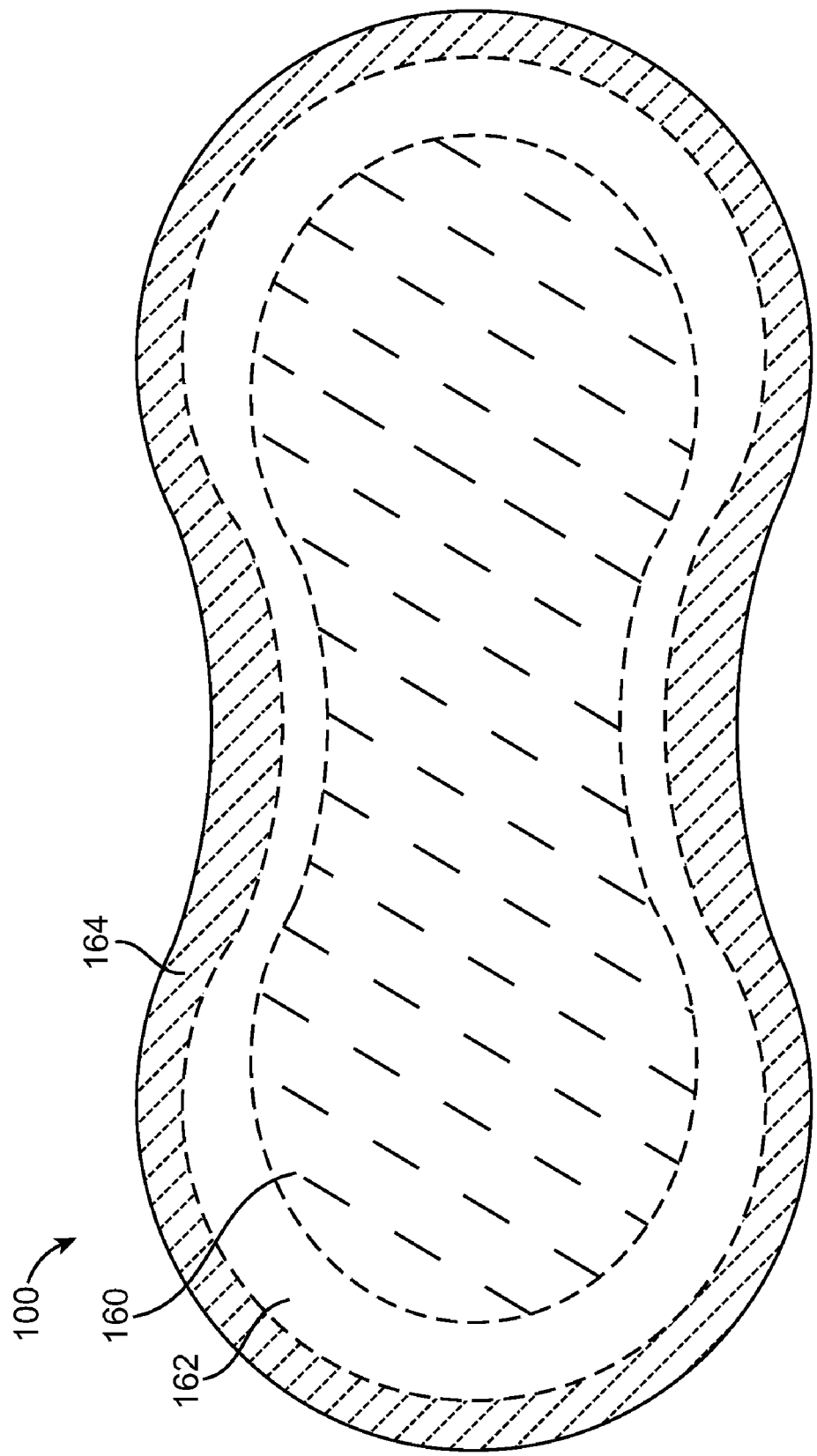
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, nylon and/or elastane (Spandex™). The breathable fabric may be coated to make it water resistant, waterproof, and/or to aid in wicking moisture away from the patch.

Figure 1H:
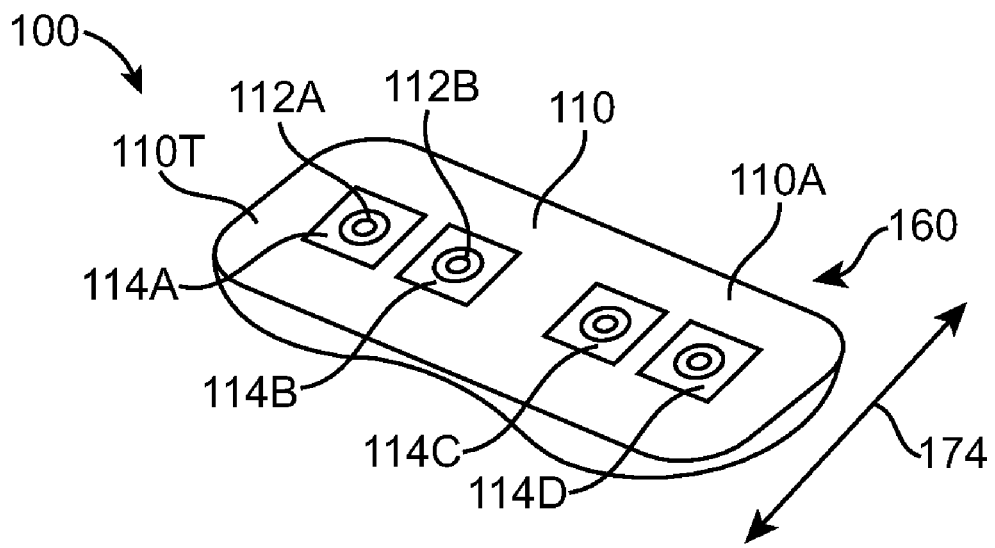
FIG. 1H shown a bottom isometric view of the adherent device as in FIGS. 1A to 1G.
Figure 1G:
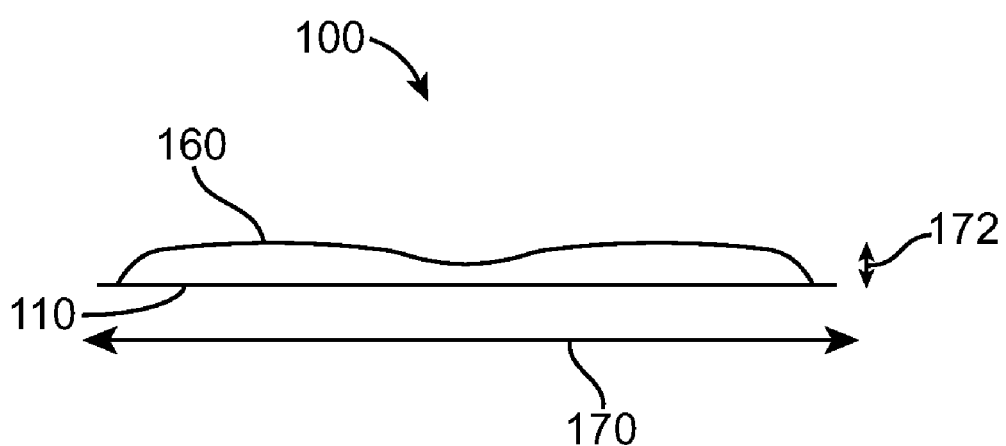
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.2 inches to about 0.6 inches (from about 5 mm to about 15 mm), from about 0.2 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 1J:
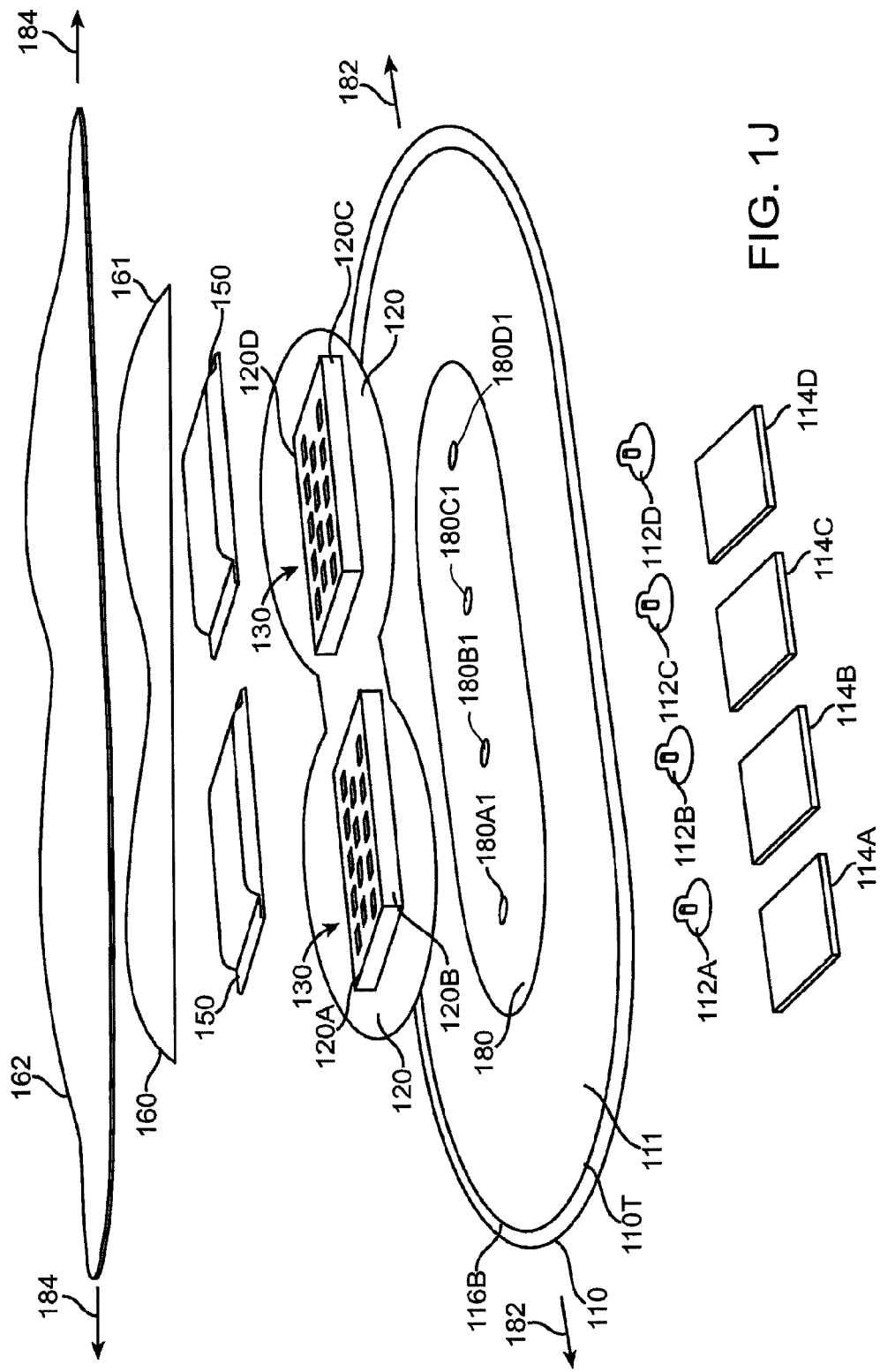

FIGS. 1I and 1J show a side cross-sectional view and an exploded view, respectively, of adherent device 100 as in FIGS. 1A to 1H. In many embodiments, device 100 comprises several layers.

FIGS. 1I1 and 1J1 show a side cross-sectional view and an exploded view, respectively, of embodiments of the adherent device with a temperature sensor affixed to the gel cover. In these embodiments, gel cover 180 extends over a wider area than in the embodiments shown in FIGS. 1I and 1J. Temperature sensor 177 is disposed over a peripheral portion of gel cover 180. Temperature sensor 177 can be affixed to gel cover 180 such that the temperature sensor can move when the gel cover stretches and tape stretch with the skin of the patient. Temperature sensor 177 may be coupled to temperature sensor circuitry 144 through a flex connection comprising at least one of wires, shielded wires, non-shielded wires, a flex circuit, or a flex PCB. This coupling of the temperature sensor allows the temperature near the skin to be measured though the breathable tape and the gel cover. The temperature sensor can be affixed to the breathable tape, for example through a cutout in the gel cover with the temperature sensor positioned away from the gel pads. A heat flux sensor can be positioned near the temperature sensor, for example to measure heat flux through to the gel cover, and the heat flux sensor coupled to heat flux circuitry similar to the temperature sensor.

The adherent device comprises electrodes 112A1, 112B1, 112C1 and 112D1 configured to couple to tissue through apertures in the breathable tape 110T. Electrodes 112A1, 112B1, 112C1 and 112D1 can be fabricated in many ways. For example, electrodes 112A1, 112B1, 112C1 and 112D1 can be printed on a flexible connector 112F, such as silver ink on polyurethane. Breathable tape 110T comprise apertures 180A1, 180B1, 180C1 and 180D1. Electrodes 112A1, 112B1, 112C1 and 112D1 are exposed to the gel through apertures 180A1, 180B1, 180C1 and 180D1 of breathable tape 110T. Gel 114A, gel 114B, gel 114C and gel 114D can be positioned over electrodes 112A1, 112B1, 112C1 and 112D1 and the respective portions of breathable tape 110T proximate apertures 180A1, 180B1, 180C1 and 180D1, so as to couple electrodes 112A1, 112B1, 112C1 and 112D1 to the skin of the patient. The flexible connector 112F comprising the electrodes can extend from under the gel cover to the printed circuit board to connect to the printed circuit boards and/or components supported thereon. For example, flexible connector 112F may comprise flexible connector 122A to provide strain relief, as described above.

In many embodiments, gel 114A, or gel layer, comprises a hydrogel that is positioned on electrode 112A to provide electrical conductivity between the electrode and the skin. In many embodiments, gel 114A comprises a hydrogel that provides a conductive interface between skin and electrode, so as to reduce impedance between electrode/skin interface. In many embodiments, gel may comprise water, glycerol, and electrolytes, pharmacological agents, such as beta blockers, ace inhibitors, diuretics, steroid for inflammation, antibiotic, antifungal agent. In specific embodiments the gel may comprise cortisone steroid. The gel layer may comprise many shapes, for example, square, circular, oblong, star shaped, many any polygon shapes. In specific embodiments, the gel layer may comprise at least one of a square or circular geometry with a dimension in a range from about 0.005" to about 0.100", for example within a range from about 0.015"-0.070", in some embodiments within a range from about 0.015"-0.040", and in specific embodiments within a range from about 0.020"-0.040". In many embodiments, the gel layer of each electrode comprises an exposed surface area to contact the skin within a range from about 100 mm^2 to about 1500 mm^2, for example a range from about 250 mm^2 to about 750 mm^2, and in specific embodiments within a range from about 350 mm^2 to about 650 mm^2. Work in relation with embodiments of the present invention suggests that such dimensions and/or exposed surface areas can provide enough gel area for robust skin interface without excessive skin coverage. In many embodiments, the gel may comprise an adhesion to skin, as may be tested with a 1800 degree peel test on stainless steel, of at least about 3 oz/in, for example an adhesion within a range from about 5-10 oz/in. In many embodiments, a spacing between gels is at least about 5 mm, for example at least about 10 mm. Work in relation to embodiments of the present invention suggests that this spacing may inhibit the gels from running together so as to avoid crosstalk between the electrodes. In many embodiments, the gels comprise a water content within a range from about 20% to about 30%, a volume resistivity within a range from about 500 to 2000 ohm-cm, and a pH within a range from about 3 to about 5.

In many embodiments, the electrodes, for example electrodes 112A to 112D, may comprise an electrode layer. A 0.001"-0.005" polyester strip with silver ink for traces can extend to silver/silver chloride electrode pads. In many embodiments, the electrodes can provide electrical conduction through hydrogel to skin, and in some embodiments may be coupled directly to the skin. Although at least 4 electrodes are shown, some embodiments comprise at least two electrodes, for example 2 electrodes. In some embodiments, the electrodes may comprise at least one of carbon-filled ABS plastic, silver, nickel, or electrically conductive acrylic tape. In specific embodiments, the electrodes may comprise at least one of carbon-filled ABS plastic, Ag/AgCl. The electrodes may comprise many geometric shapes to contact the skin, for example at least one of square, circular, oblong, star shaped, polygon shaped, or round. In specific embodiments, a dimension across a width of each electrodes is within a range from about 002" to about 0.050", for example from about 0.010 to about 0.040". In many a surface area of the electrode toward the skin of the patient is within a range from about 25 mm^2 to about 1500 mm^2, for example from about 75 mm^2 to about 150 mm^2. In many embodiments, the electrode comprises a tape that may cover the gel near the skin of the patient. In specific embodiments, the two inside electrodes may comprise force, or current electrodes, with a center to center spacing within a range from about 20 to about 50 mm. In specific embodiments, the two outside electrodes may comprise measurement electrodes, for example voltage electrodes, and a center-center spacing between adjacent voltage and current electrodes is within a range from about 15 mm to about 35 mm. Therefore, in many embodiments, a spacing between inner electrodes may be greater than a spacing between an inner electrode and an outer electrode.

In many embodiments, adherent patch 110 may comprise a layer of breathable tape 110T, for example a known breathable tape, such as tricot-knit polyester fabric. In many embodiments, breathable tape 110T comprises a backing material, or backing 111, with an adhesive. In many embodiments, the patch adheres to the skin of the patient's body, and comprises a breathable material to allow moisture vapor and air to circulate to and from the skin of the patient through the tape. In many embodiments, the backing is conformable and/or flexible, such that the device and/or patch does not become detached with body movement. In many embodiments, backing can sufficiently regulate gel moisture in absence of gel cover. In many embodiments, adhesive patch may comprise from 1 to 2 pieces, for example 1 piece. In many embodiments, adherent patch 110 comprises pharmacological agents, such as at least one of beta blockers, ace inhibitors, diuretics, steroid for inflammation, antibiotic, or antifungal agent. In specific embodiments, patch 110 comprises cortisone steroid. Patch 110 may comprise many geometric shapes, for example at least one of oblong, oval, butterfly, dogbone, dumbbell, round, square with rounded corners, rectangular with rounded corners, or a polygon with rounded corners. In specific embodiments, a geometric shape of patch 110 comprises at least one of an oblong, an oval or round. In many embodiments, the geometric shape of the patch comprises a radius on each corner that is no less than about one half a width and/or diameter of tape. Work in relation to embodiments of the present invention suggests that rounding the corner can improve adherence of the patch to the skin for an extended period of time because sharp corners, for example right angle corners, can be easy to peel. In specific embodiments, a thickness of adherent patch 110 is within a range from about 0.001" to about 0.020", for example within a range from about 0.005" to about 0.010". Work in relation to embodiments of the present invention indicates that these ranges of patch thickness can improve adhesion of the device to the skin of the patient for extended periods as a thicker adhesive patch, for example tape, may peel more readily. In many embodiments, length 170 of the patch is within a range from about 2" to about 10", width 174 of the patch is within a range from about 1" to about 5". In specific embodiments, length 170 is within a range from about 4" to about 8" and width 174 is within a range from about 2" to about 4". In many embodiments, an adhesion to the skin, as measured with a 180 degree peel test on stainless steel, can be within a range from about 10 to about 100 oz/in width, for example within a range from about 30 to about 70 oz/in width. Work in relation to embodiments of the present invention suggests that adhesion within these ranges may improve the measurement capabilities of the patch because if the adhesion is too low, patch will not adhere to the skin of the patient for a sufficient period of time and if the adhesion is too high, the patch may cause skin irritation upon removal. In many embodiments adherent patch 110 comprises a moisture vapor transmission rate (MVTR, g/m^2/24 hrs) per American Standard for Testing and Materials E-96 (ASTM E-96) is at least about 400, for example at least about 1000. Work in relation to embodiments of the present invention suggest that MVTR values as specified above can provide improved comfort, for example such that in many embodiments skin does not itch. In some embodiments, the breathable tape 110T of adherent patch 110 may comprise a porosity (sec./100 cc/in$^2$) within a wide range of values, for example within a range from about 0 to about 200. The porosity of breathable tape 11 OT may be within a range from about 0 to about 5. The above amounts of porosity can minimize itching of the patient's skin when the patch is positioned on the skin of the patient. In many embodiments, the MVTR values above may correspond to a MVTR through both the gel cover and the breathable tape. The above MVTR values may also correspond to an MVTR through the breathable tape, the gel cover and the breathable cover. The MVTR can be selected to minimize patient discomfort, for example itching of the patient's skin.

In some embodiments, the breathable tape may contain and elute a pharmaceutical agent, such as an antibiotic, anti-inflammatory or antifungal agent, when the adherent device is placed on the patient.

In many embodiments, tape 110T of adherent patch 110 may comprise backing material, or backing 111, such as a fabric configured to provide properties of patch 110 as described above. In many embodiments backing 111 provides structure to breathable tape 110T, and many functional properties of breathable tape 11 OT as described above. In many embodiments, backing 111 comprises at least one of polyester, polyurethane, rayon, nylon, breathable plastic film; woven, nonwoven, spunlace, knit, film, or foam. In specific embodiments, backing 111 may comprise polyester tricot knit fabric. In many embodiments, backing 111 comprises a thickness within a range from about 0.0005" to about 0.020", for example within a range from about 0.005" to about 0.010".

In many embodiments, an adhesive 116A, for example breathable tape adhesive comprising a layer of acrylate pressure sensitive adhesive, can be disposed on underside 110A of patch 110. In many embodiments, adhesive 116A adheres adherent patch 110 comprising backing 111 to the skin of the patient, so as not to interfere with the functionality of breathable tape, for example water vapor transmission as described above. In many embodiments, adhesive 116A comprises at least one of acrylate, silicone, synthetic rubber, synthetic resin, hydrocolloid adhesive, pressure sensitive adhesive (PSA), or acrylate pressure sensitive adhesive. In many embodiments, adhesive 116A comprises a thickness from about 0.0005" to about 0.005", in specific embodiments no more than about 0.003". Work in relation to embodiments of the present invention suggests that these thicknesses can allow the tape to breathe and/or transmit moisture, so as to provide patient comfort.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture from penetrating into gel 114A. For example gel cover 180 can keep liquid water from penetrating though the gel cover into gel 114A, while allowing moisture vapor from the gel, for example moisture vapor from the skin, to transmit through the gel cover. The gel cover may comprise a porosity at least 200 sec./100 cc/in$^2$, and this porosity can ensure that there is a certain amount of protection from external moisture for the hydrogel.

In many embodiments, the gel cover can regulate moisture of the gel near the electrodes so as to keeps excessive moisture, for example from a patient shower, from penetrating gels near the electrodes. In many embodiments, the gel cover may avoid release of excessive moisture form the gel, for example toward the electronics and/or PCB modules. Gel cover 180 may comprise at least one of a polyurethane, polyethylene, polyolefin, rayon, PVC, silicone, non-woven material, foam, or a film. In many embodiments gel cover 180 may comprise an adhesive, for example a acrylate pressure sensitive adhesive, to adhere the gel cover to adherent patch 110. In specific embodiments gel cover 180 may comprise a polyurethane film with acrylate pressure sensitive adhesive. In many embodiments, a geometric shape of gel cover 180 comprises at least one of oblong, oval, butterfly, dogbone, dumbbell, round, square, rectangular with rounded corners, or polygonal with rounded corners. In specific embodiments, a geometric shape of gel cover 180 comprises at least one of oblong, oval, or round. In many embodiments, a thickness of gel cover is within a range from about 0.0005" to about 0.020", for example within a range from about 0.0005 to about 0.010". In many embodiments, gel cover 180 can extend outward from about 0-20 mm from an edge of gels, for example from about 5-15 mm outward from an edge of the gels.

In many embodiments, the breathable tape of adherent patch 110 comprises a first mesh with a first porosity and gel cover 180 comprises a breathable tape with a second porosity, in which the second porosity is less than the first porosity to inhibit flow of the gel through the breathable tape.

In many embodiments, device 100 includes a printed circuitry, for example a printed circuitry board (PCB) module that includes at least one PCB with electronics component mounted thereon on and the battery, as described above. In many embodiments, the PCB module comprises two rigid PCB modules with associated components mounted therein, and the two rigid PCB modules are connected by flex circuit, for example a flex PCB. In specific embodiments, the PCB module comprises a known rigid FR4 type PCB and a flex PCB comprising known polyimide type PCB. In specific embodiments, the PCB module comprises a rigid PCB with flex interconnects to allow the device to flex with patient movement. The geometry of flex PCB module may comprise many shapes, for example at least one of oblong, oval, butterfly, dogbone, dumbbell, round, square, rectangular with rounded corners, or polygon with rounded corners. In specific embodiments the geometric shape of the flex PCB module comprises at least one of dogbone or dumbbell. The PCB module may comprise a PCB layer with flex PCB 120 can be positioned over gel cover 180 and electronic components 130 connected and/or mounted to flex PCB 120 so as to comprise an electronics layer disposed on the flex PCB. In many embodiments, the adherent device may comprise a segmented inner component, for example the PCB, for limited flexibility. The printed circuit may comprise polyester film with silver traces printed thereon.

In many embodiments, the electronics layer may be encapsulated in electronics housing 160. Electronics housing 160 may comprise an encapsulant, such as a dip coating, which may comprise a waterproof material, for example silicone and/or epoxy. In many embodiments, the PCB encapsulant protects the PCB and/or electronic components from moisture and/or mechanical forces. The encapsulant may comprise silicone, epoxy, other adhesives and/or sealants. In some embodiments, the electronics housing may comprising metal and/or plastic housing and potted with aforementioned sealants and/or adhesives.

In many embodiments, the electrodes are connected to the PCB with a flex connection, for example trace 123A of flex PCB 120, so as to provide strain relive between the electrodes 112A, 112B, 112C and 112D and the PCB. In such embodiments, motion of the electrodes relative to the electronics modules, for example rigid PCB's 120A, 120B, 120C and 120D with the electronic components mounted thereon, does not compromise integrity of the electrode/hydrogel/skin contact. In some embodiments, the electrodes can be connected to the PCB and/or electronics module with a flex PCB 120, such that the electrodes and adherent patch can move independently from the PCB module. In many embodiments, the flex connection comprises at least one of wires, shielded wires, non-shielded wires, a flex circuit, or a flex PCB. In specific embodiments, the flex connection may comprise insulated, non-shielded wires with loops to allow independent motion of the PCB module relative to the electrodes.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex™) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

In specific embodiments, cover 162 comprises at least one of polyester, 5-25% elastane/spandex, polyamide fabric; silicone, a polyester knit, a polyester knit without elastane, or a thermoplastic elastomer. In many embodiments cover 162 comprises at least 400% elongation. In specific embodiments, cover 162 comprises at least one of a polyester knit with 10-20% spandex or a woven polyamide with 10-20% spandex. In many embodiments, cover 162 comprises a water repellent coating and/or layer on outside, for example a hydrophobic coating, and a hydrophilic coating on inside to wick moisture from body. In many embodiments the water repellent coating on the outside comprises a stain resistant coating. Work in relation to embodiments of the present invention suggests that these coatings can be important to keep excessive moisture from the gels near the electrodes and to remove moisture from body so as to provide patient comfort.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable breathable material connected to the breathable tape, as described above, such that both the adherent patch and cover can stretch with the skin of the patient. The breathable cover may also comprise a water resistant material. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient.

Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin. Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174.

The stretching of the adherent device 100 along length 170 and width 174 can be characterized with a composite modulus of elasticity determined by stretching of cover 162, adherent patch 110 comprising breathable tape 110T and gel cover 180. For the composite modulus of the composite fabric cover-breathable tape-gel cover structure that surrounds the electronics, the composite modulus may comprise no more than about 1 MPa, for example no more than about 0.3 MPa at strain of no more than about 5%. These values apply to any transverse direction against the skin.

The stretching of the adherent device 100 along length 170 and width 174, may also be described with a composite stretching elongation of cover 162, adherent patch 110 comprising breathable tape breathable tape 110T and gel cover 180. The composite stretching elongation may comprise a percentage of at least about 10% when 3 kg load is a applied, for example at least about 100% when the 3 kg load applied. These percentages apply to any transverse direction against the skin.

The printed circuit board may be adhered to the adherent patch 110 comprising breathable tape 110T at a central portion, for example a single central location, such that adherent patch 110 can stretch around this central region. The central portion can be sized such that the adherence of the printed circuit board to the breathable tape does not have a substantial effect of the modulus of the composite modulus for the fabric cover, breathable tape and gel cover, as described above. For example, the central portion adhered to the patch may be less than about 100 mm$^2$, for example with dimensions of approximately 10 mm by 10 mm (about 0.5" by 0.5"). Such a central region may comprise no more than about 10% of the area of patch 110, such that patch 110 can stretch with the skin of the patient along length 170 and width 174 when the patch is adhered to the patient.

The cover material may comprise a material with a low recovery, which can minimize retraction of the breathable tape from the pulling by the cover. Suitable cover materials with a low recovery include at least one of polyester or nylon, for example polyester or nylon with a loose knit. The recovery of the cover material may be within a range from about 0% recovery to about 25% recovery. Recovery can refer to the percentage of retraction the cover material that occurs after the material has been stretched from a first length to a second length. For example, with 25% recovery, a cover that is stretched from a 4 inch length to a 5 inch length will retract by 25% to a final length of 4.75 inches.

Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable breathable material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

Cover 162 may comprise many shapes. In many embodiments, a geometry of cover 162 comprises at least one of oblong, oval, butterfly, dogbone, dumbbell, round, square, rectangular with rounded corners, or polygonal with rounded corners. In specific embodiments, the geometric of cover 162 comprises at least one of an oblong, an oval or a round shape.

Cover 162 may comprise many thicknesses and/or weights. In many embodiments, cover 162 comprises a fabric weight: within a range from about 100 to about 200 g/m^2, for example a fabric weight within a range from about 130 to about 170 g/m^2.

In many embodiments, cover 162 can attach the PCB module to adherent patch 110 with cover 162, so as to avoid interaction of adherent patch 110C with the PCB having the electronics mounted therein. Cover 162 can be attached to breathable tape 110T and/or electronics housing 160 comprising over the encapsulated PCB. In many embodiments, adhesive 116B attaches cover 162 to adherent patch 110. In many embodiments, cover 162 attaches to adherent patch 110 with adhesive 116B, and cover 162 is adhered to the PCB module with an adhesive 161 on the upper surface of the electronics housing. Thus, the PCB module can be suspended above the adherent patch via connection to cover 162, for example with a gap 169 between the PCB module and adherent patch. In many embodiments, gap 169 permits air and/or water vapor to flow between the adherent patch and cover, for example through adherent patch 110 and cover 162, so as to provide patient comfort.

In many embodiments, adhesive 116B is configured such that adherent patch 110 and cover 162 can be breathable from the skin to above cover 162 and so as to allow moisture vapor and air to travel from the skin to outside cover 162. In many embodiments, adhesive 116B is applied in a pattern on adherent patch 110 such that the patch and cover can be flexible so as to avoid detachment with body movement. Adhesive 116B can be applied to upper side 110B of patch 110 and comprise many shapes, for example a continuous ring, dots, dashes around the perimeter of adherent patch 110 and cover 162. Adhesive 116B may comprise at least one of acrylate, silicone, synthetic rubber, synthetic resin, pressure sensitive adhesive (PSA), or acrylate pressure sensitive adhesive. Adhesive 16B may comprise a thickness within a range from about 0.0005" to about 0.005", for example within a range from about 0.001-0.005". In many embodiments, adhesive 116B comprises a width near the edge of patch 110 and/or cover 162 within a range from about 2 to about 15 mm, for example from about 3 to about 7 near the periphery. In many embodiments with such widths and/or thickness near the edge of the patch and/or cover, the tissue adhesion may be at least about 30 oz/in, for example at least about 40 oz/in, such that the cover remains attached to the adhesive patch when the patient moves.

In many embodiments, the cover is adhered to adherent patch 110 comprising breathable tape 110T at least about 1 mm away from an outer edge of adherent patch 110. This positioning protects the adherent patch comprising breathable tape 110T from peeling away from the skin and minimizes edge peeling, for example because the edge of the patch can be thinner. In some embodiments, the edge of the cover may be adhered at the edge of the adherent patch, such that the cover can be slightly thicker at the edge of the patch which may, in some instances, facilitate peeling of the breathable tape from the skin of the patient.

Gap 169 extend from adherent patch 110 to the electronics module and/or PCB a distance within a range from about 0.25 mm to about 4 mm, for example within a range from about 0.5 mm to about 2 mm.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin and an electrode through the breathable tape, for example with the gel.

FIGS. 2A and 2B show components of an adherent device 200 comprising an adhesive patch 210 and connection structures to provide strain relief so as to decouple the patch from an electronics module 220. Adherent device 200 comprises many structures similar to those shown above. Adherent device 200 comprises electrodes 212A, 212B, 212C and 212D affixed to adherent patch 210. Adherent device 200 may comprise a gel, for example gel 214A over the electrodes, for example over electrode 212A. Electrodes 212A, 212B, 212C and 212D are connected to electronics module 220 with structures 223A, 223B, 223C and 223D. Electronics module 220 may comprise PCB with components mounted thereon, as described above. In many embodiments, structures 223A, 223B, 223C and 223D connect adhesive patch 210 to electronics module 220 with a flexible connection. In many embodiments, structures 223A, 223B, 223C and 223D comprise curved flexible wires, for example spirals and/or loops of wire that connect electrodes 212A, 212B, 212C and 212D to an electronics module 220. Structures 223A, 223B, 223C and 223D may comprise polyester film with silver traces coupled to silver/silver chloride electrodes to provide strain relief. Adhesive patch 210 comprises a lower side 210A toward the skin of the patient and an upper side 210B away from the skin of the patient. Adhesive 216B is disposed on upper side 210B of patch 210 to connect the adhesive patch to a cover, as described above. Electronics module 220 can be connected to the cover, as described above, such that module 220 is suspended above adhesive patch 210 with a gap 269. Gap 269 can decouple movement between patch 210 and electronic module 220. In many embodiments, gap 260 allows adhesive patch 210 and/or device 200 to breath, for example from the skin through the patch and cover to the outside of the cover, as described above.

In many embodiments, gap 269 can extend from adherent patch 210 to the electronics module 220 and/or PCB a distance within a range from about 0.25 mm to about 4 mm, for example within a range from about 0.5 mm to about 2 mm.

While the exemplary embodiments have been described in some detail, by way of example and for clarity of understanding, those of skill in the art will recognize that a variety of modifications, adaptations, and changes may be employed.

Hence, the scope of the present invention should be limited solely by the appended claims.

What is claimed is:

1. An adherent device to monitor a patient for an extended period, the device comprising:
   a breathable tape comprising a porous material with an adhesive coating to adhere the breathable tape to a skin of the patient;
   at least one electrode affixed to the breathable tape and capable of electrically coupling to a skin of the patient;
   a printed circuit board connected to the breathable tape to support the printed circuit board with the breathable tape when the tape is adhered to the patient;
   electronic components electrically connected to the printed circuit board and coupled to the at least one electrode to measure physiologic signals of the patient;
   an electronics housing adhered to at least one of the electronics components or the printed circuit board; and
   a breathable cover disposed over the circuit board and electronic components such that the electronics housing is disposed between the cover and electronics components, wherein the breathable cover is connected to at least one of the electronics components, the printed circuit board or the breathable tape.

2. The adherent device of claim 1 wherein the printed circuit board is connected to the breathable tape with an intermediate connector.

3. The adherent device of claim 1 further comprising a gap extending between the breathable tape and the printed circuit board.

4. The adherent device of claim 3 wherein the gap extends between the breathable tape and printed circuit board for a distance from about 0.25 mm to about 4 mm to allow the tape to breathe under the printed circuit board when the tape is adhered to the patient.

5. The adherent device of claim 1 wherein the breathable cover comprises a stretchable material.

6. The adherent device of claim 5 wherein the stretchable material comprises at least one of polyester fabric, nylon or polyamide fabric.

7. The adherent device of claim 5 wherein the stretchable material comprises from about 5% to about 25% elastane fabric.

8. The adherent device of claim 5 wherein the stretchable material comprises at least about 100% elongation.

9. The adherent device of claim 5 wherein the stretchable material comprises an elastomeric material comprising at least about 400% elongation.

10. The adherent device of claim 1 wherein the breathable cover comprises at least one of a water repellant outside coating to repel water or hydrophilic inside coating to wick moisture away from the skin of the patient.

11. The adherent device of claim 10 wherein the breathable cover comprises the water repellant outside coating and the hydrophilic inside coating.

12. The adherent device of claim 1 wherein the breathable cover comprises fabric weight from about 100 to 200 grams per square meter.

13. The adherent device of claim 1 further comprising a flexible connection structure to couple the electrodes to the printed circuit board so as to relieve strain between the electrodes and the printed circuit board.

14. The adherent device of claim 13 wherein the printed circuit board is adhered to the breathable tape at a central location and wherein the breathable tape is configured to stretch with the skin of the patient away from the central location.

15. The adherent device of claim 13 wherein the flexible connection structure supports the printed circuit board with a gap between the printed circuit board and the breathable tape.

16. The adherent device of claim 13 wherein the flexible connection structure comprises at least one of shielded wires, non-shielded wires, a flexible printed circuit board or polyester film with silver printing.

17. The adherent device of claim 1 wherein the breathable tape comprises a flexible material and a thickness from about 0.005" to about 0.010".

18. The adherent device of claim 1 wherein the breathable tape comprises a backing, and the backing comprises a polyester knit fabric and a thickness from about 0.005" to about 0.010".

19. The adherent device of claim 1 wherein the breathable tape comprises an acrylate pressure sensitive adhesive on an underside of the tape, the adhesive having a thickness less than about 0.004" to allow the tape to breath when the adhesive is applied to the patient.

20. The adherent device of claim 1 wherein the electronics housing comprises a waterproof encapsulant to protect the printed circuit board and the electronic components from moisture and/or mechanical forces.

21. The adherent device of claim 1 further comprising a gel cover positioned over the breathable tape to inhibit a flow of a gel through the breathable tape and wherein the printed circuit board is located over the gel cover such that the gel cover is disposed between the breathable tape and the printed circuit board.

22. The adherent device of claim 21 wherein the gel cover comprises at least one of a polyurethane film or polyurethane non-woven backing and an acrylate pressure sensitive adhesive.

23. The adherent device of claim 21 wherein the gel cover comprises a porosity of at least about 200 sec./100 cc/in^2 to protect the gel from external moisture.

24. The adherent device of claim 21 wherein an edge of the gel cover extends from about 5 to about 15 mm beyond an edge of a gel over the at least one electrode.

25. The adherent device of claim 21 wherein the breathable tape comprises a knit polyester fabric backing and the gel cover comprises a polyurethane, film backing.

26. The adherent device of claim 21 wherein the breathable tape comprises a first porosity and wherein the gel cover comprises a breathable tape with a second porosity, the second porosity less than the first porosity to inhibit flow of the gel through the breathable tape having the first porosity.

27. The adherent device of claim 21 wherein breathable tape, the at least one electrode, the gel cover, and the gel are separable from the printed circuit board, the electronic components, the breathable cover, and the electronics housing, such that the printed circuit board, the electronic components, the breathable cover, and electronics housing are reusable.

28. The adherent device of claim 1 wherein the at least one electrode extends through at least one aperture in the breathable tape.

29. The adherent device of claim 1 further comprising at least one gel disposed over a contact surface of the at least one electrode to electrically connect the electrode to the skin.

30. The adherent device of claim 1 wherein the at least one electrode is configured to electrically couple to the printed circuit board through the breathable tape.

31. The adherent device of claim 1 further comprising an adhesive disposed around the breathable tape to connect the cover to the breathable tape.

32. The adherent device of claim 1 wherein the breathable tape comprises an MVTR of at least about 400 g/m$^2$/24 hrs.

33. The adherent device of claim 32 further comprising a gel cover positioned over the breathable tape and wherein an MVTR through the breathable tape and the gel cover comprises at least about 400 g/m$^2$/24 hrs.

34. The adherent device of claim 33 wherein an MVTR through the breathable tape, the gel cover and the breathable cover comprises at least about 400 g/m$^2$/24 hrs.

35. The adherent device of claim 1, wherein the breathable cover fits loosely over the electronics housing, such that a portion of the breathable cover can move with respect to the electronics housing.

36. The adherent device of claim 35, wherein the electronics housing is smooth, such that the breathable cover is slidably coupled with the electronics housing.

37. The adherent device of claim 1, wherein the electronic components include wireless communications circuitry that transmits at least one physiologic signal to a remote server.

38. The adherent device of claim 37, wherein the electronic components comprise impedance circuitry, and wherein the wireless communications circuitry is coupled to the impedance circuitry to transmit to the remote server a hydration signal derived from an output of the impedance circuitry.

39. The adherent device of claim 37, wherein the electronic components comprise electrocardiogram circuitry, and wherein the wireless communications circuitry is coupled to the electrocardiogram circuitry to transmit to the remote server an electrocardiogram signal derived from an output of the electrocardiogram circuitry.

40. The adherent device of claim 37, wherein the electronic components comprise an accelerometer, and wherein the wireless communications circuitry is coupled to the accelerometer to transmit to the remote server an inclination signal derived from an output of the accelerometer.

\* \* \* \* \*